(12) United States Patent
Best et al.

(10) Patent No.: US 7,446,103 B2
(45) Date of Patent: Nov. 4, 2008

(54) BICYCLIC BENZAMIDE COMPOUND AS HISTAMINE H3 RECEPTOR LIGAND USEFUL IN THE TREATMENT OF NEUROLOGICAL DISEASES

(75) Inventors: Desmond John Best, Harlow (GB); Barry Sidney Orlek, Harlow (GB)

(73) Assignee: Glaxo Group Limited, Brentford, Middlesex (GB)

( * ) Notice: Subject to any disclaimer, the term of this patent is extended or adjusted under 35 U.S.C. 154(b) by 461 days.

(21) Appl. No.: 10/532,373

(22) PCT Filed: Oct. 20, 2003

(86) PCT No.: PCT/EP03/11650

§ 371 (c)(1), (2), (4) Date: Apr. 21, 2005

(87) PCT Pub. No.: WO2004/037788

PCT Pub. Date: May 6, 2004

(65) Prior Publication Data

US 2007/0105838 A1    May 10, 2007

(30) Foreign Application Priority Data

Oct. 22, 2002    (GB)    .................. 0224557.9
Mar. 19, 2003    (GB)    .................. 0306328.6

(51) Int. Cl.
| A61K 31/47 | (2006.01) |
| A61K 31/55 | (2006.01) |
| C07D 403/02 | (2006.01) |
| C07D 215/08 | (2006.01) |

(52) U.S. Cl. .................. 514/217.01; 514/307; 514/311; 514/415; 540/594; 546/139; 546/152; 548/469

(58) Field of Classification Search ........................ None
See application file for complete search history.

(56) References Cited

U.S. PATENT DOCUMENTS

| 4,916,128 A | * | 4/1990 | Jonas et al. | ............. | 514/213.01 |
| 5,496,844 A | * | 3/1996 | Inai et al. | .................... | 514/415 |

FOREIGN PATENT DOCUMENTS

| EP | 1262475 A1 | 12/2002 |
| JP | 9221476 | 8/1997 |
| WO | WO9534540 | 12/1995 |
| WO | WO9840385 | 9/1998 |
| WO | WO9850363 | 11/1998 |
| WO | WO9850364 | 11/1998 |
| WO | WO0006254 | 2/2000 |
| WO | WO0123374 | 4/2001 |
| WO | WO0166520 | 9/2001 |
| WO | WO0166534 | 9/2001 |
| WO | WO0212190 | 2/2002 |
| WO | WO0224695 | 3/2002 |
| WO | WO02076925 | 10/2002 |
| WO | WO02094788 | 11/2002 |
| WO | 2004026305 A1 | 4/2004 |
| WO | 2004035544 A1 | 4/2004 |
| WO | 2004035556 A1 | 4/2004 |
| WO | 2004037800 A1 | 5/2004 |

OTHER PUBLICATIONS

Adock et al., "Substituent Effects of $^{19}$F Nuclear Magnetic Resonance: Polar and π-Electron Effects", Aust. J. Chem 29:2571-2581 (1976).
Austin et al., "Novel 2,3,4,5-Tetrahydro-1H-3-benzazepines with High Affinity and Selectivity for the Dopamine$_3$ Receptor", Bioorg Med Chem Lett 10:2553-2555 (2000).
Austin et al., "Design and Synthesis of Novel 2,3-Dihydro-1H-isoindoles with High Affinity and Selectivity for the Dopamine $D_3$ Receptor," Bioorg Med Chem Lett 11:685-688 (2001).
Frankel, Chemische Berichte vol. 33 pp. 2811 (1900).
Giovannini et al., "Effects of histamine $H_3$ receptor agonista and antagonists on cognitive performance and scopolamine-induced amnesia," Behavirural Brain Res. 104:147-155 (1999).
Leurs et al., "Therapeutic potential of histamine $H_3$ receptor agonists and antagonists," TiPS 19:177-183 (May 1998).
Lovenberg et al., "Cloning and Funcational Expression of the Human Histamine $H_3$ Receptor," Molecular Pharmacology 55:1101-1107 (1999).
Onodera and Watanabe, "Histamine $H_3$ Antagonists as Potential Therapeutics in the CNS," ed Leurs and Timmerman, pp. 255-267, Elsevier Science B.V. (1998).
Rice et al., "Synthesis of Fluorinated Derivatives of Benzo[k]fluoranthene and indeno[1,2,3-cd]pyrene and 8,9-Dihydro-8,9-epoxybenzo[k]fluoranthene," J. Org. Chem 53:1775-1779 (1988).
Schlicker et al., "Modulation of neurotransmitter release via histamine $H_3$ heteroreceptors," Fundam Clin Pharmacol 8:128-137 (1994).
Stokker, "Preparation of 1,2,3.4-Tetrahydroisoquinolines Lacking Electron Donating Groups—An Intramolecular Cyclization Complementary to the Pictet-Spengler Reaction," Tetrahedron Letters 37(31):5453-5456 (1996).
Walsh et al., "Synthesis and Antiallergy Activity of 4-(Diarylhydroxymethyl)-1-[3-(aryloxy)propyl]piperidines and Structurally Related Compounds," J. Med. Chem 32:105-118 (1989).
Weinstock et al., "Synthesis and Renal Vasodilator Activity of Some Dopamine Agonist 1-Aryl-2,3,4,5-tetrahydro-1H-3-benzazepine-7,8-diols: Halogen and Methyl Analogues of Fenoldopam," J. Med. Chem 29:2315-2325 (1986).

* cited by examiner

*Primary Examiner*—Zinna N Davis
(74) *Attorney, Agent, or Firm*—Bonnie L. Deppenbrock

(57) ABSTRACT

The present invention relates to novel bicyclic benzamide derivatives having pharmacological activity, processes for their preparation, to compositions containing them and to their use in the treatment of neurological and psychiatric disorders.

11 Claims, No Drawings

BICYCLIC BENZAMIDE COMPOUND AS HISTAMINE H3 RECEPTOR LIGAND USEFUL IN THE TREATMENT OF NEUROLOGICAL DISEASES

CROSS-REFERENCE TO RELATED APPLICATIONS

This application is filed pursuant to 35 U.S.C. § 371 as a U.S. National Phase Application of International Application No. PCT/EP2003/011650 filed Oct. 20, 2003, which claims priority from GB0224557.9 filed Oct. 22, 2002 and GB0306328.6 filed Mar. 19, 2003.

FIELD OF THE INVENTION

The present invention relates to novel bicyclic benzamide derivatives having pharmacological activity, processes for their preparation, to compositions containing them and to their use in the treatment of neurological and psychiatric disorders.

BACKGROUND OF THE INVENTION

WO 02/76925 (Eli Lilly), WO 00/06254 (Societe Civile Bioprojet), WO 01/66534 (Abbott Laboratories) and WO 02/12190 (Ortho McNeil Pharmaceutical Inc) describe a series of compounds which are claimed to be histamine H3 antagonists. WO 02/094788 (Eli Lilly and Company) describe a series of substituted tetrahydroquinoline derivatives which are claimed to be useful in the treatment of diseases associated with aberrant physiological responses to endogenous estrogen. WO 01/23374 (SmithKline Beecham plc) describe a series of piperazine derivatives as 5-HT1B antagonists which are claimed to be useful in the treatment of CNS disorders. WO 98/40385 (Novo Nordisk) describe a series of tetrahydrothienopyridine derivatives which are claimed to be useful in diseases related to glucose metabolic pathways. WO 95/34540 and JP 09221476 (both Otsuka Pharm Co) describe a series of benzoheterocyclic derivatives as vasopressin or oxytocin modulators which are claimed to be useful in a variety of disorders. WO 01/66520 (Ono Pharm Co) describe a series of indole derivatives as prostaglandin D antagonists which are claimed to be useful in allergic diseases, pruritus and cerebrovascular disease.

The histamine H3 receptor is predominantly expressed in the mammalian central nervous system (CNS), with minimal expression in peripheral tissues except on some sympathetic nerves (Leurs et al., (1998), Trends Pharmacol. Sci. 19, 177-183). Activation of H3 receptors by selective agonists or histamine results in the inhibition of neurotransmitter release from a variety of different nerve populations, including histaminergic and cholinergic neurons (Schlicker et al., (1994), Fundam. Clin. Pharmacol. 8, 128-137). Additionally, in vitro and in vivo studies have shown that H3 antagonists can facilitate neurotransmitter release in brain areas such as the cerebral cortex and hippocampus, relevant to cognition (Onodera et al., (1998), In: The Histamine H3 receptor, ed Leurs and Timmerman, pp 255-267, Elsevier Science B.V.). Moreover, a number of reports in the literature have demonstrated the cognitive enhancing properties of H3 antagonists (e.g. thioperamide, clobenpropit, ciproxifan and GT-2331) in rodent models including the five choice task, object recognition, elevated plus maze, acquisition of novel task and passive avoidance (Giovanni et al., (1999), Behav. Brain Res. 104, 147-155). These data suggest that novel H3 antagonists and/or inverse agonists such as the current series could be useful for the treatment of cognitive impairments in neurological diseases such as Alzheimer's disease and related neurodegenerative disorders.

SUMMARY OF THE INVENTION

The present invention provides, in a first aspect, a compound of formula (I) or a pharmaceutically acceptable salt thereof:

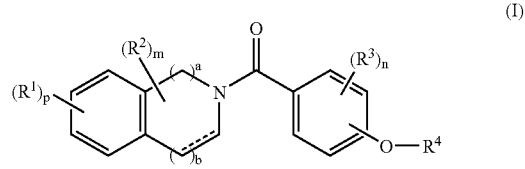

wherein:

$R^1$ and $R^2$ independently represent halogen, hydroxy, cyano, nitro, oxo, haloC$_{1-6}$ alkyl, polyhaloC$_{1-6}$ alkyl, haloC$_{1-6}$ alkoxy, polyhaloC$_{1-6}$ alkoxy, C$_{1-6}$ alkyl, C$_{1-6}$ alkoxy, arylC$_{1-6}$ alkoxy, C$_{1-6}$ alkylthio, C$_{1-6}$ alkoxyC$_{1-6}$ alkyl, C$_{3-7}$ cycloalkylC$_{1-6}$ alkoxy, C$_{1-6}$ alkanoyl, C$_{1-6}$ alkoxycarbonyl, aryl, heteroaryl, heterocyclyl, arylC$_{1-6}$ alkyl, heteroarylC$_{1-6}$ alkyl, heterocyclylC$_{1-6}$ alkyl, C$_{1-6}$ alkylsulfonyl, C$_{1-6}$ alkylsulfinyl, C$_{1-6}$ alkylsulfonyloxy, C$_{1-6}$ alkylsulfonylC$_{1-6}$ alkyl, arylsulfonyl, arylsulfonyloxy, arylsulfonylC$_{1-6}$ alkyl, aryloxy, —CO-aryl, —CO-heterocydyl, —CO-heteroaryl, C$_{1-6}$ alkylsulfonamidoC$_{1-6}$ alkyl, C$_{1-6}$ alkylamidoC$_{1-6}$ alkyl, arylsulfonamido, arylaminosulfonyl, arylsulfonamidoC$_{1-6}$ alkyl, arylcarboxamidoC$_{1-6}$ alkyl, aroylC$_{1-6}$ alkyl, arylC$_{1-6}$ alkanoyl, or a group NR$^{15}$R$^{16}$, —NR$^{15}$CO-aryl, —NR$^{15}$CO-heterocyclyl, —NR$^{15}$CO-heteroaryl, —CONR$^{15}$R$^{16}$, —NR$^{15}$COR$^{16}$, —NR$^{15}$SO$_2$R$^{16}$ or —SO$_2$NR$^{15}$R$^{16}$, wherein R$^{15}$ and R$^{16}$ independently represent hydrogen or C$_{1-6}$ alkyl; wherein said aryl, heteroaryl and heterocyclyl groups of R$^1$ and R$^2$ may be optionally substituted by one or more (eg. 1, 2 or 3) substituents which may be the same or different and which are selected from halogen, C$_{1-6}$ alkyl, C$_{1-6}$ alkoxy, oxo, CF$_3$, OCF$_3$, CN, C$_{1-6}$ alkanoyl, C$_{1-6}$ alkylsulfonyl, C$_{1-6}$ alkylsulfonyloxy, C$_{1-6}$ alkylamido or C$_{1-6}$ alkylsulfonamido;

a and b independently represent 0, 1 or 2, such that a and b cannot both represent 0;

----- is a single or double bond;

R$^3$ represents halogen, C$_{1-6}$ alkyl, C$_{1-6}$ alkoxy, cyano, amino or trifluoromethyl;

m and n independently represent 0, 1 or 2;

p represents an integer from 0 to 3, such that when p is an integer greater than 1, two R$^1$ groups may instead be linked to form a heterocyclyl group;

R$^4$ represents —(CH$_2$)$_q$—NR$^{11}$R$^{12}$ or a group of formula (i):

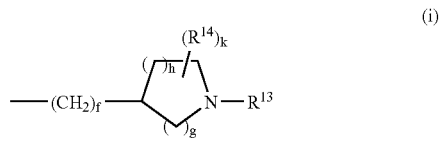

wherein q is 2, 3 or 4;

R$^{11}$ and R$^{12}$ independently represent C$_{1-6}$ alkyl or together with the nitrogen atom to which they are attached represent an N-linked heterocyclic group optionally substituted by one or two R$^{17}$ groups;

R$^{13}$ represents hydrogen, C$_{1-6}$ alkyl, C$_{3-8}$ cycloalkyl, —C$_{1-6}$ alkyl-aryl or heterocyclyl;

$R^{14}$ and $R^{17}$ independently represent halogen, $C_{1-6}$ alkyl, halo$C_{1-6}$ alkyl, OH, di$C_{1-6}$ alkylamino or $C_{1-6}$ alkoxy;

f and k independently represent 0, 1 or 2;

g is 0, 1 or 2 and h is 0, 1, 2 or 3, such that g and h cannot both be 0;

or solvates thereof.

DETAILED DESCRIPTION

In one particular aspect of the present invention, when a represents 0, b represents 2, ----- is a single bond and m represents 1, $R^2$ represents a group other than optionally substituted phenyl.

In another particular aspect of the present invention, when $R^4$ represents a group of formula (i), f represents 0 and p represents 1, $R^1$ represents a group other than optionally substituted piperazinyl.

In another particular aspect of the present invention, when $R^4$ represents 4-morpholinylethyl or pyrrolidinylmethyl, m represents 1 and ----- is a single bond, $R^2$ represents a group other than $C_{1-6}$ alkyl or optionally substituted aryl.

In another particular aspect of the present invention, when a represents 0, b represents 2 or 3 and $R^4$ is a group other than pyrrolidinylalkyl.

In another particular aspect of the present invention, there is provided a compound of formula (I) as defined above wherein a represents 0, b represents 1 and p represents 1, $R^1$ is a group other than $C_{1-6}$ alkoxycarbonyl, $C_{1-6}$ alkylamido$C_{1-6}$ alkyl or CONR$^{15}$R$^{16}$.

Alkyl groups, whether alone or as part of another group, may be straight chain or branched and the groups alkoxy and alkanoyl shall be interpreted similarly. The term 'halogen' is used herein to describe, unless otherwise stated, a group selected from fluorine, chlorine, bromine or iodine and the term 'polyhalo' is used herein to refer to a moiety containing more than one (eg. 2-5) of said halogen atoms.

The term "aryl" includes single and fused rings wherein at least one ring is aromatic, for example, phenyl, naphthyl and tetrahydronaphthalenyl.

The term "heterocyclyl" is intended to mean a 4-7 membered monocyclic saturated or partially unsaturated aliphatic ring containing 1 to 3 heteroatoms selected from oxygen or nitrogen. Suitable examples of such monocyclic rings include pyrrolidinyl, piperidinyl, piperazinyl, morpholinyl, 1,3-dioxolane, diazepanyl and azepanyl.

The term "heteroaryl" is intended to mean a 5-7 membered monocyclic aromatic or a fused 8-11 membered bicyclic aromatic ring containing 1 to 3 heteroatoms selected from oxygen, nitrogen and sulphur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused aromatic rings include benzofused aromatic rings such as quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like.

Preferably, m represents 0 or 1, more preferably 0.

Preferably, p represents 0, 1 or 2, more preferably 0 or 1, especially 0.

When present, $R^1$ is preferably halogen (eg. fluorine, bromine or chlorine), hydroxy, cyano, nitro, —NR$^{15}$R$^{16}$ (eg. NH$_2$), —NR$^{15}$COR$^{16}$ (eg. —NH-acetyl), polyhalo$C_{1-6}$ alkyl (eg. CF$_3$), heterocyclyl (eg. pyrrolidinyl optionally substituted by one or two oxo groups), $C_{1-6}$ alkyl (eg. methyl), $C_{1-6}$ alkoxy (eg. methoxy), $C_{1-6}$ alkylsulfonyl (eg. —SO$_2$Me), $C_{1-6}$ alkylsulfinyl (eg. —SOMe), $C_{1-6}$ alkanoyl (eg. —COMe), arylsulfonamido (eg. —NHSO$_2$Ph), arylaminosulfonyl (eg. —SO$_2$NHPh), —NR$^{15}$SO$_2$R$^{16}$ (eg. —NHSO$_2$Me), —SO$_2$NR$^{15}$R$^{16}$ (eg. SO$_2$N(Me$_2$)) or —CO-heterocyclyl (eg. —CO-morpholinyl or —CO-pyrrolidinyl).

In one preferred embodiment, p represents 2 and both $R^1$ groups are linked to form a heterocyclyl group (eg. 1,3-dioxolane).

When present, $R^1$ is more preferably halogen (eg. fluorine) or cyano, especially fluorine.

When present, $R^2$ is preferably $C_{1-6}$ alkyl (eg. methyl), aryl$C_{1-6}$ alkyl (eg. benzyl), aryl (eg. phenyl optionally substituted by one or more OMe or isopropylSO$_2$ groups) or heteroaryl (eg. thienyl).

When present, $R^3$ is preferably halogen (eg. chlorine) or polyhalo$C_{1-6}$ alkyl (eg. 2-CF$_3$), more preferably chlorine (eg. 2-chlorine).

When b is 0, a is preferably 1, when b is 1, a is preferably 0, 1 or 2 and when b is 2, a is preferably 0.

More preferred compounds of formula (I) are those wherein a is 1 and b is 0 or 1 or a is 0 and b is 1.

Especially preferred compounds of formula (I) are those wherein a is 1 and b is 0.

Preferably, ----- is a single bond.

Preferably, n represents 0 or 1, more preferably 0.

Preferably, —O—R$^4$ is present on the phenyl group at the 4-position.

When R$^4$ represents a group of formula (i), preferably, f represents 0, h represents 1, g represents 2, k represents 0 and R$^{13}$ represents $C_{1-6}$ alkyl (eg. isopropyl) or $C_{3-8}$ cycloalkyl (eg. cyclobutyl). More preferably, when R$^4$ represents a group of formula (i), f represents 0, h represents 1, g represents 2, k represents 0 and R$^{13}$ represents $C_{3-8}$ cycloalkyl (eg. cyclobutyl).

Preferably, R$^4$ represents —(CH$_2$)$_q$—NR$^{11}$R$^{12}$.

Preferably, q is 3.

Preferably, NR$^{11}$R$^{12}$ represents a heterocyclic group, more preferably unsubstituted piperidine.

Preferred compounds according to the invention include examples E1-E65 as shown below, or a pharmaceutically acceptable salt thereof.

More preferred compounds according to the invention include:

N-[4-(3-Piperidin-1-ylpropoxy)benzoyl]isoindoline;

N-[4-(3-Piperidin-1-ylpropoxy)-benzoyl]-5-fluoroisoindoline;

N-{4-[(1-Cyclobutyl4-piperidinyl)oxy]benzoyl}isoindoline; and

N-{4-[(1-Cyclobutyl-4-piperidinyl)oxy]benzoyl}-5-fluoroisoindoline;

or a pharmaceutically acceptable salt thereof.

An especially preferred compound according to the invention is N-[4-(3-piperidin-1-ylpropoxy)benzoyl]isoindoline or a pharmaceutically acceptable salt thereof.

Compounds of formula (I) may form acid addition salts with acids, such as conventional pharmaceutically acceptable acids, for example maleic, hydrochloric, hydrobromic, phosphoric, acetic, fumaric, salicylic, sulphate, citric, lactic, mandelic, tartaric and methanesulphonic. Salts, solvates and hydrates of histamine H3 receptorantagonists or inverse agonists therefore form an aspect of the invention.

Certain compounds of formula (I) are capable of existing in stereoisomeric forms. It will be understood that the invention encompasses all geometric and optical isomers of these compounds and the mixtures thereof including racemates. Tautomers also form an aspect of the invention.

The present invention also provides a process for the preparation of a compound of formula (I) or a pharmaceutically acceptable salt thereof, which process comprises:

(a) reacting a compound of formula (II)

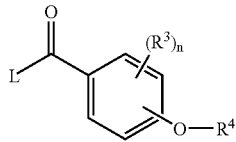

with a compound of formula (III)

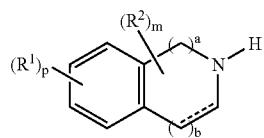

or a protected derivative thereof, wherein $R^1$, $R^2$, $R^3$, $R^4$, a, b, m, n and p are as defined above and L is OH or a suitable leaving group (eg. a halogen atom such as chlorine); or (b) preparing a compound of formula (I) wherein $R^4$ represents $-(CH_2)_q-NR^{11}R^{12}$ which comprises reacting a compound of formula (IV)

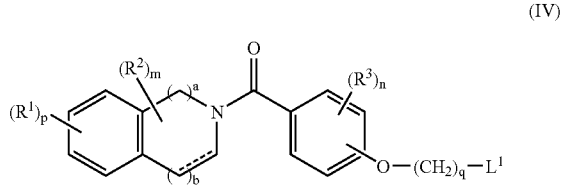

wherein $R^1$, $R^2$, $R^3$, a, b, m, n, p and q are as defined above and $L^1$ represents a suitable leaving group such as a halogen atom (eg. bromine) with a compound of formula $HNR^{11}R^{12}$; wherein $R^{11}$ and $R^{12}$ are as defined above; and optionally thereafter (c) deprotecting a compound of formula (I) which is protected; and optionally thereafter (d) interconversion to other compounds of formula (I).

Process (a) typically comprises halogenation of the compound of formula (II) with a suitable halogenating agent (eg. thionyl chloride) followed by reaction with the compound of formula (III) in the presence of a suitable base such as triethylamine or a solid supported amine, in a suitable solvent such as dichloromethane. Process (a) may also typically comprise activation of the compound of formula (II) with a coupling reagent such as dicyclohexylcarbodiimide or solid supported carbodiimide in a suitable solvent such as N,N-dimethylformamide followed by reaction with the compound of formula (III). Alternatively process (a) may involve activation of (II) by formation of a suitable ester such as a pentachlorophenyl ester followed by reaction with an N-benzyl protected analogue of (III) in the presence of poly(methylhydrosiloxane) and palladium hydroxide in a suitable solvent such as isopropanol.

Process (b) is typically performed in the presence of a suitable solvent (such as 1-butanol) at an elevated temperature.

In process (c), examples of protecting groups and the means for their removal can be found in T. W. Greene 'Protective Groups in Organic synthesis' (J. Wiley and Sons, 1991). Suitable amine protecting groups include sulphonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl ($-COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (d) may be performed using conventional interconversion procedures such as epimerisation, oxidation, reduction, alkylation, nucleophilic or electrophilic aromatic substitution, ester hydrolysis or amide bond formation.

Compounds of formula (II) wherein $R^4$ represents $-(CH_2)_q-NR^{11}R^{12}$ may be prepared in accordance with the following procedure:

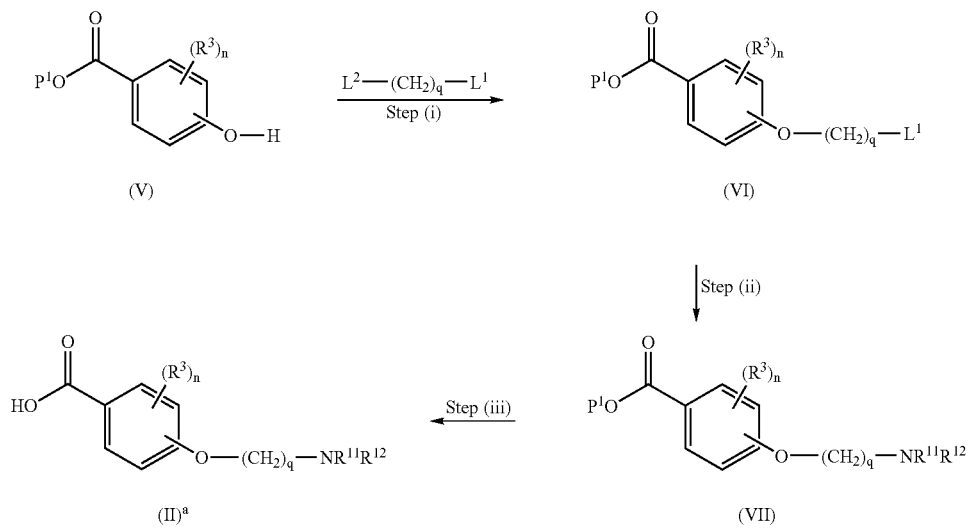

wherein $R^3$, n, q, $R^{11}$ and $R^{12}$ are as defined above, $P^1$ represents a protecting group such as methyl, ethyl or t-butyl, $L^1$ and $L^2$ independently represent a leaving group such as halogen (eg. $L^1$ represents chlorine and $L^2$ represents bromine). The —$CO_2H$ group of compounds of formula (II)$^a$ may be converted to —COL wherein L represents a leaving group by, for example, halogenation using thionyl chloride.

Step (i) typically comprises reaction of a compound of formula (V) with a suitable alkylating agent such as 1-bromo-3chloropropane in a suitable solvent such as acetone in the presence of potassium carbonate.

Step (ii) typically comprises treatment of a compound of formula (VI) with an amine of formula $HNR^{11}R^{12}$.

Step (iii) comprises a deprotection reaction which may be performed for example under acidic conditions with hydrochloric acid.

Compounds of formula (IV) may be prepared by hydrolysing a compound of formula (VI) as defined above under suitable conditions (eg. under acidic conditions with HCl), suitably activated (eg. by conversion into the acid chloride with thionyl chloride), followed by treatment with a compound of formula (III) as defined above.

Compounds of formula (II) wherein $R^4$ represents —$(CH_2)_q$—$NR^{11}R^{12}$ may also be prepared in accordance with the following procedure:

to be of potential use in the treatment of neurological diseases including Alzheimer's disease, dementia, age-related memory dysfunction, mild cognitive impairment, cognitive deficit, epilepsy, neuropathic pain, inflammatory pain, migraine, Parkinson's disease, multiple sclerosis, stroke and sleep disorders including narcolepsy; psychiatric disorders including schizophrenia (particularly cognitive deficit of schizophrenia), attention deficit hyperactivity disorder, depression and addiction; and other diseases including obesity, asthma, allergic rhinitis, nasal congestion, chronic obstructive pulmonary disease and gastrointestinal disorders.

Thus the invention also provides a compound of formula (I) or a pharmaceutically acceptable salt thereof, for use as a therapeutic substance in the treatment or prophylaxis of the above disorders, in particular cognitive impairments in diseases such as Alzheimer's disease and related neurodegenerative disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt

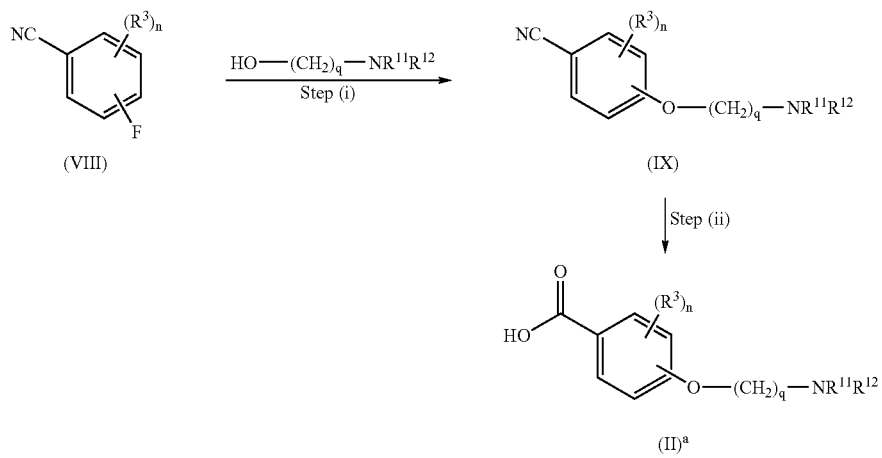

wherein $R^3$, n, q, $R^{11}$ and $R^{12}$ are as defined above.

Step (i) typically comprises reaction of a compound of formula (VIII) in the presence of a suitable base such as sodium hydride in an appropriate solvent such as dimethylsulfoxide or N,N-dimethylformamide.

Step (ii) typically comprises a hydrolysis reaction for example under acidic conditions using hydrochloric acid.

Compounds of formula (IV) may be prepared using an analogous procedure using HO—$(CH_2)_q$-$L^3$, wherein q is as defined above and $L^3$ represents an OH group or a group convertible to a leaving group.

Compounds of formula (II) wherein $R^4$ represents a group of formula (i) may be prepared in a similar manner to the procedure shown above.

Compounds of formula (III), (V) and (VIII) are either known in the literature or can be prepared by analogous methods.

Compounds of formula (I) and their pharmaceutically acceptable salts have affinity for and are antagonists and/or inverse agonists of the histamine H3 receptor and are believed thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt thereof and a pharmaceutically acceptable carrier.

The present invention further provides a pharmaceutical composition which comprises the compound of formula (I) or a pharmaceutically acceptable salt thereof and a pharmaceutically acceptable carrier.

Compounds of formula (I) may be used in combination with other therapeutic agents, for example histamine H1 antagonists or medicaments claimed to be useful as either disease modifying or symptomatic treatments of Alzheimer's disease. Suitable examples of such other therapeutic agents may be agents known to modify cholinergic transmission such as 5-$HT_6$ antagonists, M1 muscarinic agonists, M2 muscarinic antagonists or acetylcholinesterase inhibitors. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Descriptions and Examples illustrate the preparation of compounds of the invention.

Description 1 (Method A)

Ethyl 4-(3-Piperidin-1-ylpropoxy)benzoate (D1)

A stirred mixture of ethyl 4-(3-chloropropoxy)benzoate (4.73 g) (D. A. Walsh et al J. Med. Chem. 1989, 32(1), 105), piperidine (2.9 ml), sodium carbonate (3.1 g) and potassium iodide (162 mg) in 1-butanol (50 ml) was heated at 105° C. for 16 h. The reaction was cooled to rt, diluted with EtOAc (100 ml), washed with water (3×50 ml), saturated brine (50 ml), dried ($MgSO_4$) and evaporated to give the title compound (D1) (6.88 g). MS electrospray (+ion) 292 ($MH^+$). $^1$H NMR δ ($CDCl_3$): 7.98 (2H, d, J=8.8 Hz), 6.90 (2H, d, J=8.8 Hz), 4.34 (2H, q, J=7.5 Hz), 4.06 (2H, t, J=6.3 Hz), 2.46 (4H, m), 2.00 (2H, m), 1.50 (6H, m), 1.38 (3H, t, J=7.5 Hz).

Description 1 (Method B)

Ethyl 4-(3-Piperidin-1-ylpropoxy)benzoate (D1)

Step 1: Ethyl 4-(3-chloropropoxy)benzoate

Ethyl 4-hydroxybenzoate (60.0 g), 1-bromo-3-chloropropane (71.37 ml) and potassium carbonate (149.61 g) were heated under reflux in acetone (1445 ml) overnight. The reaction mixture was then allowed to cool to rt, filtered and evaporated. The residue was chromatographed [silica gel; step gradient 0-5% ethyl acetate/hexane]. Fractions containing pure product were combined and evaporated to give the subtitled compound as a clear oil (70.0 g). MS electrospray (+ion) 243 ($MH^+$). $^1$H NMR δ ($CDCl_3$): 8.00 (2H, d, J=8.8 Hz), 6.92 (2H, d, J=8.8 Hz), 4.36 (2H, q, J=7.1 Hz), 4.18 (2H, t, J=5.8 Hz), 3.74 (2H, t, J=6.2), 2.25 (2H, m), 1.37 (3H, t, J=7.1 Hz).

Step 2: Ethyl 4-(3-Piperidin-1-ylpropoxy)benzoate

A stirred mixture of ethyl 4-(3-chloropropoxy)benzoate (70.0 g), piperidine (43.35 ml), sodium carbonate (45.36 g) and potassium iodide (2.37 g) in 1-butanol (650 ml) was heated at 105° C. for 16 h. The reaction was cooled to rt, diluted with EtOAc (1600 ml), washed with water (3×700 ml), saturated brine (700 ml), dried ($MgSO_4$) and evaporated to give the title compound (D1) (82.57 g) which displayed MS and $^1$H NMR spectra that were identical to those of the product obtained by D1 (Method A).

Description 2 (Method A)

4-(3-Piperidin-1-ylpropoxy)benzoic acid hydrochloride (D2)

A solution of ethyl 4-(3-piperidin-1-ylpropoxy)benzoate (D1) (1.4 g) in concentrated hydrochloric acid (15 ml) was heated under reflux for 1 h, cooled and evaporated to give the title compound (D2) (1.02 g). MS electrospray (+ion) 264 ($MH^+$). $^1$H NMR δ (DMSO-d6): 10.59 (1H, s), 10.25 (1H, s), 7.90 (2H, d, J=9 Hz), 7.02 (2H, d, J=9 Hz), 4.14 (2H, t, J=6 Hz), 3.05-3.52 (4H, m), 2.91 (2H, m), 2.20 (2H, m), 1.25-1.91 (6H, m).

Description 2 (Method B)

4-(3-Piperidin-1-ylpropoxy)benzoic acid hydrochloride (D2)

A solution of ethyl 4-(3-piperidin-1-ylpropoxy)benzoate (D1) (82.57 g) in concentrated hydrochloric acid (750 ml) was heated under reflux for 2 h. The mixture was cooled to rt then chilled to 5° C. and filtered. The filter cake was washed with acetone and dried to yield the title compound (D2) as a white crystalline solid (75.30 g) that displayed MS and $^1$H NMR spectra that were identical to those of the product obtained by D2 (Method A).

Description 3

4-(3-Piperidin-1-ylpropoxy)benzoyl chloride hydrochloride (D3)

4-(3-Piperidin-1-ylpropoxy)benzoic acid hydrochloride (D2) (0.23 g) in thionyl chloride (5 ml) was heated under reflux for 1 h. The reaction mixture was then evaporated to a minimum and co-evaporated from DCM (3×10 ml) to give the title compound (D3) as a white powder (0.24 g).

Description 4

4-3-Piperidin-1-yl-propoxy)-2-trifluoromethyl-benzonitrile (D4)

4-Fluoro-2-trifluoromethyl-benzonitrile (1.20 g) was dissolved in THF (20 ml) and 3-piperidin-1-yl-propan-1-ol (0.91 ml) was added. The reaction was cooled to 0° C. and potassium hexamethyidisilazide (0.5M solution in toluene; 12.72 ml) was added dropwise. The reaction was stirred at rt overnight, then diluted with ethyl acetate (50 ml) and partitioned with aqueous 1N HCl (50 ml). The aqueous layer was washed with ethyl acetate (50 ml), then basified to pH 8.0 with sodium hydrogen carbonate and extracted with ethyl acetate (3×75 ml). The combined organic extracts were dried (MgSO$_4$) and evaporated to give the title compound (D4) as a clear oil which crystallised on standing (0.80 g).

Description 5

4-(3-Piperidin-1-yl-propoxy)-2-trifluoromethyl-benzoic acid (D5)

4-(3-Piperidin-1-yl-propoxy)-2-trifluoromethyl-benzonitrile (D4) (0.80 g) was dissolved in conc. HCl (20 ml) and heated at 135° C. for 24 h. Concentrated sulfuric acid (10 ml) was added and the reaction heated at 135° C. for 36 h. The reaction mixture was then evaporated to a minimum and treated with 12.5 N sodium hydroxide solution until pH 12 was obtained. The mixture was filtered and the filtrate evaporated to a minimum. Conc. HCl was then added until pH 1. The mixture was evaporated and the solid residue was extracted several times with methanol. The combined extracts were evaporated to give the title compound (D5) as a white solid (0.90 g).

Description 6

4-(3-Piperidin-1-yl-propoxy)-2-trifluoromethyl-benzoyl chloride (D6)

4-(3-Piperidin-1-yl-propoxy)-2-trifluoromethyl-benzoic acid (D5) (0.9 g) was heated at reflux in thionyl chloride (20 ml) for 2 h. The reaction mixture was evaporated to a minimum then co-evaporated with DCM (3×) to give the title compound (D6) as a white solid (1.0 g)

Description 7

N-Benzyl-5-fluoroisoindoline (D7)

A solution of benzylamine (64.3 ml) and triethylamine (164 ml) in toluene (1 L) was added to 1,2-bis(bromomethyl)-4-fluorobenzene (164.1 g) (*J. Org. Chem.*, 1988, 53, 1775-9). This mixture was heated to reflux for 4 h under argon. The reaction mixture was then filtered and the solid was washed with toluene (3×150 ml). The filtrate was evaporated in vacuo and the residue dissolved in dichloromethane (1 L). This solution was washed successively with a saturated solution of potassium carbonate (1 L) and water (0.5 L). The organic extract was dried (MgSO$_4$), concentrated to a volume of 0.5 L and cooled in ice. The unwanted precipitate was filtered off and the filtrate evaporated to a residue which was purified by chromatography over silica gel eluting with a gradient of dichloromethane/ethyl acetate to give the title compound (D7) as an oil (49.3 g). MS electrospray (+ion) 228 (MH$^+$). $^1$H NMR δ (CDCl$_3$): 7.24-7.42 (5H, m), 7.07-7.12 (1H, m), 6.82-6.89 (2H, m), 3.89 (6H, br, s).

Description 8

5-Fluoroisoindoline hydrochloride (D8)

A suspension of 20% palladium hydroxide on carbon (4.0 g) and N-benzyl-5-fluoroisoindoline (D7) (44.6 g) in ethanol (475 ml) and conc. hydrochloric acid (d=1.18, 25 ml) was stirred with hydrogen at 50 psi for 18 h at 45° C. The mixture was cooled to ambient temperature and filtered to remove the catalyst. The filtrate was evaporated in vacuo to give a solid which was stirred with acetone (300 ml) for 0.5 h and filtered to give the title compound (D8) as a solid (29.3 g). $^1$H NMR δ (D6-DMSO): 10.0 (2H, br, s), 7.41-7.46 (1H, m), 7.15-7.29 (2H, m), 4.49 (2H, s), 4.46 (2H, s).

Description 9

N-Benzyl-4-fluoroisoindoline (D9)

3-Fluoroxylene (5.67 g) was converted to the title compound (D9) (5 g) using the method described in D7 for N-benzyl-5-fluoroisoindoline. MS electrospray (+ion) 228 (MH$^+$). $^1$H NMR δ (CDCl$_3$): 6.82-7.42 (8H, m), 3.99 (2H, s), 3.95 (2H, s), 3.91 (2H, s).

Description 10

Pentachlorophenyl 4-(3-piperidin-1-ylpropoxy)benzoate (D10)

A stirred suspension of 4-(3-piperidin-1-ylpropoxy)benzoic acid hydrochloride (D2) (1 g) in DCM (10 ml) at rt was treated with oxalyl chloride (0.58 ml) and 10% DMF in DCM (3 drops). After 1 h the solution was evaporated and then re-evaporated from DCM (2×10 ml). The acid chloride was redissolved in DCM (20 ml) and treated with pentachlorophenol (0.89 g) and triethylamine (1.02 ml), then stirred for 4 h and evaporated. The residue was redissolved in EtOAc (20 ml), washed with 5% sodium carbonate solution (10 ml), water (2×10 ml), brine (10 ml), dried (MgSO$_4$) and evaporated to yield the title compound (D10) (1.2 g). MS electrospray (+ion) 228 (MH$^+$). $^1$H NMR δ (CDCl$_3$): 6.82-7.42 (8H, m), 3.99 (2H, s), 3.95 (2H, s), 3.91 (2H, s).

Description 11

N-Benzyl-5-methoxycarbonylisoindoline (D11)

4-Methoxycarbonylxylene (5.16 g) was converted to the title compound (D11) (4.5 g) using the method described in D7 for N-benzyl-5-fluoroisoindoline. MS electrospray (+ion) 268 (MH+). $^1$H NMR δ (CDCl$_3$): 7.14-7.91 (8H, m), 3.96 (2H, s), 3.92 (2H, s), 3.89 (2H, s)

Description 12

N-t-Butoxycarbonyl-5-methoxycarbonylisoindoline (D12)

A mixture of di t-butyldicarbonate (0.9 g) and N-benzyl-5-methoxycarbonylisoindoline (D11) (200 mg) in EtOH (10 ml) at rt was treated with poly(methylhydrosiloxane) (0.67 ml) and palladium hydroxide on carbon (50 mg, 20% Pd) and stirred overnight. The mixture was filtered and evaporated. The residue was chromatographed on a silica gel flash column [step gradient 5-20% EtOAc in light petroleum 40-60] to give the title compound (D12) (0.64 g). MS electrospray (+ion) 278 (MH+). $^1$H NMR δ (CDCl$_3$): 7.94 (2H, m), 7.32 (1H, m), 4.72 (2H, s), 4.68 (2H, s), 3.92 (3H, s), 1.52 (9H, s).

Description 13

N-t-Butoxycarbonyl-5-carboxyisoindoline (D13)

A solution of N-t-butoxycarbonyl-5-methoxycarbonyl-isoindoline (D12) (2.11 g) in MeOH (10 ml) was treated with 1M NaOH and heated at 60° C. for 1 h. The mixture was cooled to rt and the MeOH evaporated. The aqueous was washed with diethyl ether (2×20 ml), then acidified with 5% citric acid solution and extracted with diethyl ether (2×20 ml). The combined extracts were washed with water (2×20 ml), brine (20 ml), dried (MgSO$_4$) and evaporated to give the title compound (D13) (1.47 g). MS electrospray (+ion) 264 (MH+). $^1$H NMR δ (CDCl$_3$): 8.02 (2H, m), 7.35 (1H, m), 4.75 (2H, s), 4.71 (2H, s), 1.53 (9H, s).

Description 14

N-t-Butoxycarbonyl-5-aminocarbonylisoindoline (D14)

A mixture of N-t-butoxycarbonyl-5-carboxyisoindoline (D13) (240 mg), EDC (350 mg), HOBT (140 mg), triethylamine (0.32 ml) and 0.880 ammonia solution (1 ml) in DMF (10 ml) was stirred overnight at rt and then evaporated. The residue was partitioned between EtOAc (10 ml) and 5% citric acid (10 ml). The organic layer was collected, washed with water (10 ml), saturated NaHCO$_3$ solution (10 ml), water (10 ml), brine (10 ml), dried (MgSO$_4$) and evaporated to give the title compound (D14) (154 mg). MS electrospray (+ion) 263 (MH+). $^1$H NMR δ (CDCl$_3$), 7.73 (2H, m), 7.26 (1H, m), 6.88 (2H, m), 4.72 (2H, s), 4.69 (2H, s),1.52 (9H, s).

Description 15

N-t-Butoxycarbonyl-5-cyanoisoindoline (D15)

A solution of N-t-butoxycarbonyl-5-aminocarbonylisoin-doline (D14) (140 mg) in pyridine (3 ml) at rt was treated with 4-toluenesulfonyl chloride (305 mg) and then stirred overnight. Following evaporation the residue was dissolved in EtOAc (10 ml), washed with saturated NaHCO$_3$ solution (10 ml), water (10 ml), brine (10 ml), dried (MgSO$_4$) and concentrated. The residue was chromatographed on a silica gel flash column [step gradient 5-20% EtOAc in light petroleum 40-60] to give the title compound (D15) (0.64 g). MS electrospray (+ion) 189 (MH+-t-Bu). $^1$H NMR δ (CDCl$_3$): 7.56 (2H, m), 7.38 (1H, m), 4.71 (4H, m), 1.52 (9H, s).

Description 16

5-Cyanoisoindoline trifluoroacetate (D16)

A solution of N-t-butoxycarbonyl-5-cyanoisoindoline (D15) (130 mg) in DCM (3 ml) at rt was treated with TFA (1 ml) and after 1 h it was evaporated. The residue was re-evaporated from MeOH/toluene to give the title compound (D16) (140 mg). $^1$H NMR δ (CDCl$_3$): 7.70 (2H, m), 7.50 (1H, m), 4.75 (4H, m).

Description 17

N-t-Butoxycarbonyl-5-[(pyrrolidin-1-yl)carbonyl] isoindoline (D17)

A mixture of N-t-butoxycarbonyl-5-carboxyisoindoline (D13) (300 mg), EDC (440 mg), HOAT (10 mg), triethylamine (0.4 ml) and pyrrolidine (0.11 ml) in DCM (10 ml) was stirred overnight and then evaporated. The residue was redissolved in EtOAc (10 ml), washed with saturated NaHCO$_3$ solution (10 ml), water (10 ml), brine (10 ml), dried (MgSO$_4$) and evaporated. The residue was chromatographed on a silica gel flash column [step gradient 70-90% EtOAc in light petroleum 40-60] to give the tiUe compound (D17) (314 mg). MS electrospray (+ion) 317 (MH+). $^1$H NMR δ (CDCl$_3$): 7.42 (2H, m), 7.27 (1H, m), 4.70 (2H, m), 4.67 (2H, m), 3.65 (2H, m), 3.42 (2H, m), 1.92 (4H, m), 1.52

Description 18

5-[(Pyrrolldin-1-yl)carbonyl]isoindoline hydrochloride (D18)

A solution of N-t-butoxycarbonyl-5-[(pyrrolidin-1-yl)car-bonyl]isoindoline (D17) (300 mg) in DCM (5 ml) at rt was treated with 4M HCl in dioxan (1 ml) for 1 h and then evaporated. The residue was triturated with acetone to give the title compound (D18) (85 mg). MS electrospray (+ion) 217 (MH+). $^1$H NMR δ(DMSO-d6): 9.95 (1H, m), 7.58 (3H, m), 4.52 (2H, m), 3.46 (2H, m), 1.84 (4H, m).

Description 19

N-t-Butoxycarbonyl-5-[(morpholin-4-yl)carbonyl] isoindoline (D19)

A mixture of N-t-butoxycarbonyl-5-carboxyisoindoline (D13) (300 mg), EDC (440 mg), HOAT (10 mg), triethylamine (0.4 ml) and morpholine (0.12 ml) in DCM (10 ml) was stirred overnight and then evaporated. The residue was redissolved in EtOAc (10 ml), washed with saturated NaHCO$_3$ solution (10 ml), water (10 ml), brine (10 ml), dried (MgSO$_4$) and evaporated. The residue was chromatographed on a silica gel flash column [step gradient 70-90% EtOAc in light petroleum 40-60] to give the title compound (D19) (314 mg). MS electrospray (+ion) 333 (MH+). $^1$H NMR δ (CDCl$_3$): 7.30 (3H, m), 4.70 (2H, m), 4.67 (2H, m), 3.70 (8H, m), 1.52 (9H, s).

Description 20

5-[(Morpholin-4-yl)carbonyl]isoindoline trifluoroacetate (D20)

A solution of N-t-butoxycarbonyl-5-[(morpholin-4-yl)car-bonyl] isoindoline (D19) (300 mg) in DCM (5 ml) at rt was treated with TFA (2 ml) for 1 h and then evaporated. The residue was re-evaporated from DCM/toluene to give the title compound (D20) (305 mg). MS electrospray (+ion) 233 (MH⁺). $^1$H NMR δ (CDCl$_3$): 10.10 (1H, m), 7.25 (3H, m), 4.64 (2H, m), 4.53 (2H, m), 3.54 (8H, m).

Description 21

4-[(1-tert-Butoxycarbonyl-4-piperidinyl)oxy]benzonitrile (D21)

4-Fluorobenzonitrile (3.0 g) was dissolved in THF (50 ml) and then N-tert-butoxy-carbonyl-4-piperidinol (4.98 g) was added. Potassium hexamethyidisilazide (20% wt solution in THF, 24.62 g) was then added dropwise and the reaction stirred at rt for 2 h. The reaction mixture was then evaporated to a minimum, redissolved in EtOAc (100 ml) and washed with aqueous 1 N HCl (2×100 ml), saturated sodium bicarbonate solution (2×100 ml) and brine (100 ml). The organic layer was dried (MgSO$_4$) and then purified by chromatography [silica gel, step gradient 0-60% EtOAc/Hexane]. Fractions containing the required product were evaporated to give the title compound (D21) as a clear oil which crystallised on standing (6.83 g). $^1$H NMR δ (CDCl$_3$): 7.59 (2H, d, J=7.50 Hz), 6.95 (2H, d, J=7.50 Hz), 4.44 (1H, m), 3.70 (2H, m), 3.38 (2H, m), 1.91 (2H, m), 1.77 (2H, m). 1.47 (9H, s).

Description 22

4-(4-Piperidinyloxy)benzonitrile trifluoroacetate (D22)

4-[(1-tert-Butoxycarbonyl-4-piperidinyl)oxy]benzonitrile (D21) (6.83 g) was dissolved in DCM (30 ml) and TFA (30 ml) was added. The reaction was stirred at rt for 1 h and then evaporated to give the title compound (D22) as a yellow oil (7.15 g—TFA salt plus 1.3 equivalents of TFA).

Description 23

4-[(1-Cyclobutyl-4-piperidinyl)oxy]benzonitrile (D23)

4-(4-Piperidinyloxy)benzonitrile trifluoroacetate (D22) (2.2 g) was dissolved in DCM (50 ml) and triethylamine (1.92 ml) was added followed by cyclobutanone (0.64 g). The mixture was stirred for 5 min, then sodium triacetoxyborohydride (1.94 g) was added and the reaction was stirred at rt under argon overnight. The reaction mixture was then washed with saturated potassium carbonate solution (3×30 ml) and brine (30 ml). The organic layer was dried (MgSO$_4$) and evaporated to give the title compound (D23) as a white solid (1.91 g). $^1$H NMR δ (CDCl$_3$): 7.56 (2H, d, J=6.84 Hz), 6.93 (2H, d, J=6.80 Hz), 4.41 (1H, m), 2.77 (1H, m), 2.75 (2H, m), 2.30 (2H, m), 2.06 (4H, m), 1.87 (4H, m), 1.66 (2H, m).

Description 24

4-[(1-Cyclobutyl-4-piperidinyl)oxy]benzoic acid hydrochloride (D24)

4-[(1-Cyclobutyl-4-piperidinyl)oxy]benzonitrile (D23) (1.91 g) was dissolved in conc. HCl (30 ml) and heated to 120° C. for 2 h. The reaction mixture was then allowed to cool to rt and then further cooled to 5° C. The resultant white precipitate was filtered off and washed with a small quantity of water. The solid was then dried at 50° C. under vacuum overnight to yield the title compound (D24) as a white powder (0.95 g). $^1$H NMR δ (DMSO-d6): 12.60 (1H, s), 10.96 (1H, s), 7.90 (2H, d, J=8.70 Hz), 7.09 (2H, d, J=8.60 Hz), 4.09-4.64 (1H, m), 3.66-3.15 (3H, m), 2.99-2.77 (2H, m), 2.48-1.60 (10H, m).

Description 25

4-[(1-Cyclobutyl-4-piperidinyl)oxy]benzoyl chloride hydrochloride (D25)

4-[(1-Cyclobutyl-4-piperidinyl)oxy]benzoic acid hydrochloride (D24) (0.20 g) was dissolved in thionyl chloride (10 ml) and heated under reflux for 1.5 h. The thionyl chloride was removed by evaporation and the residue evaporated from DCM (3×10 ml) to give the title compound (D25) (0.21 g).

Description 26

2-Chloro-4-(3-piperidin-1-ylpropoxy)benzonitrile (D26)

2-Chloro-4-fluorobenzonitrile (5.0 g) and 3-(1-piperidinyl)-1-propanol (3.4 g) were stirred in DMSO (70 ml) at rt under argon. Sodium hydride (60% wt in mineral oil, 1.976 g) was then added and the reaction stirred at rt for 5 h. The reaction mixture was diluted with ethyl acetate (200 ml), washed with saturated sodium hydrogen carbonate (100 ml), water (3×100 ml), brine (100 ml), dried (MgSO$_4$) and evaporated. The crude product was then purified by column chromatography [silica gel, step gradient 0-10% MeOH (containing 10% 0.880 ammonia solution) in DCM)] and fractions containing pure product were combined and evaporated to give the title compound (D26) as a white solid (6.29 g). MS electrospray (+ion) 279/281 (MH⁺).

Description 27

2-Chloro-4-(3-piperidin-1-ylpropoxy)benzoic acid hydrochloride (D27)

2-Chloro-4-(3-piperidin-1-ylpropoxy)benzonitrile (D26) (6.29 g) with aqueous 1M sodium hydroxide (45.2 ml) in ethanol (60 ml) was heated at reflux for 72 h. The reaction mixture was then evaporated to remove ethanol and the aqueous solution treated with excess conc. hydrochloric acid and heated at 120° C. for 2 h. The reaction mixture was then cooled to 5° C. and filtered. The filter cake was washed with a small volume of water and then acetone followed by drying at 65° C. under high vacuum overnight to give the title compound (D27) as a pale brown powder (6.48 g). MS electrospray (+ion) 298/230 (MH⁺). $^1$H NMR δ (DMSO-d6): 13.05 (1H, s), 10.85 (1H, s), 7.89 (1H, d, J=8.7 Hz), 7.10 (1H, s), 7.02 (1H, d, J=8.7 Hz), 4.16 (2H, t, J=6.0 Hz), 3.40 (2H, m), 3.13 (2H, m), 2.88 (2H, m), 2.23 (2H, m), 1.94-1.35 (6H, m).

Description 28

2-Chloro-4-(3-piperidin-1-ylpropoxy)benzoyl chloride hydrochloride (D28)

2-Chloro-4-(3-piperidin-1-ylpropoxy)benzoic acid hydrochloride (D27) (1.0 g) was heated at reflux in thionyl chloride (20 ml) for 1.5 h. The thionyl chloride was removed by evaporation and the residue evaporated from DCM (3×30 ml) to give the title compound (D28) (1.0 g).

Description 29

2-Chloro-4-[(1-tert-butoxycarbonyl-4-piperidinyl)oxy]benzonitrile (D29)

The title compound (D29) was obtained as a white solid (5.0 g) using the procedure described in D21 except that 2-chloro-4-fluorobenzonitrile (2.66 g) was used. ¹H NMR δ (CDCl₃): 7.57 (1H, d, J=8.72 Hz), 7.01 (1H, s), 6.86 (1H, d, J=8.72 Hz), 4.55 (1H, m), 3.69 (2H, m), 3.38 (2H, m), 1.93 (2H, m), 1.78 (2H, m), 1.47 (9H, s).

Description 30

2-Chloro-4-(4-piperidinyloxy)benzonitrile hydrochloride (D30)

2-Chloro-4-[(1-tert-butoxycarbonyl-4-piperidinyl)oxy]benzonitrile (D29) (5.0 g) was dissolved in methanol (150 ml) and 4N HCl in dioxane (100 ml) was added. The reaction stirred at rt overnight. The reaction mixture was then evaporated to give the title compound (D30) as a white solid (4.0 g).

Description 31

2-Chloro-4-[(1-isopropyl-4-piperidinyl)oxy]benzonitrile (D31)

2-Chloro-4-(4-piperidinyloxy)benzonitrile hydrochloride (D30) (1.5 g) was dissolved in DCM (40 ml) and triethylamine (2.29 ml) was added followed by acetone (0.64 g). The mixture was stirred for 5 min and then sodium triacetoxyborohydride (1.94 g) was added and the reaction stirred at rt under argon overnight. The reaction mixture was then washed with saturated potassium carbonate solution (2×40 ml) and brine (40 ml). The organic layer was dried (MgSO₄) and evaporated to give the title compound (D31) as a white solid (1.51 g). MS electrospray (+ion) 279 (MH⁺).

Description 32

2-Chloro-4-[(1-isopropyl-4-piperidinyl)oxy]benzoic acid hydrochloride (D32)

2-Chloro-4-[(1-isopropyl-4-piperidinyl)oxy]benzonitrile (D31) (1.51 g) was dissolved in conc. HCl and heated at 125° C. for 72 h with additional conc. HCl (10 ml) added every 2 h 4 times a day. The reaction mixture was then evaporated to a minimum (co-evaporated with toluene (3×30 ml) then MeOH/toluene (1:1 vol, 2×30 ml). The residue was dissolved in methanol and acetone was added until a precipitate (ammonium chloride) formed which was filtered off. The filtrate was evaporated to a minimum and dried at 50° C. under vacuum overnight to yield the title compound (D32) as a white powder (1.66 g). MS electrospray (+ion) 298 (MH⁺).

Description 33

2-Chloro-4-[(1-isopropyl-4-piperidinyl)oxy]benzoyl chloride hydrochloride (D33)

2-Chloro-4-[(1-isopropyl-4-piperidinyl)oxy]benzoic acid hydrochloride (D32) (0.20 g) was dissolved in thionyl chloride (10 ml) and heated under reflux for 1.5 h. The thionyl chloride was removed by evaporation and the residue was evaporated from DCM (3×10 ml) to give the title compound (D33) (0.21 g).

Description 34

2-Chloro-4-[(1-cyclobutyl-4-piperidinyl)oxy]benzonitrile (D34)

The title compound (D34) was obtained as a white solid (1.56 g) using the procedure of D23 except that 2-chloro-4-(4-piperidinyloxy)benzonitrile hydrochloride (D30) (1.5 g) was used. ¹H NMR δ (CDCl₃): 7.57 (1H, d, J=8.73 Hz), 6.99 (1H, s), 6.87 (2H, d, J=8.80) 4.43 (1H, m), 2.76 (1H, m), 2.60 (2H, m), 2.28 (2H, m), 2.15-1.58 (10H, m).

Description 35

2-Chloro-4-[(1-cyclobutyl-4-piperidinyl)oxy]benzoic acid hydrochloride (D35)

2-Chloro-4-[(1-cyclobutyl-4-piperidinyl)oxy]benzonitrile (D34) (1.56 g) was dissolved in conc. HCl and heated at 125° C. for 72 h with additional conc. HCl (10 ml) added every 2 h 4 times a day. The reaction mixture was then evaporated to a minimum (co-evaporated with toluene (3×30 ml) then MeOH/toluene (1:1 vol 2×30 ml). The residue was dissolved in methanol, and acetone was added until a precipitate (ammonium chloride) formed which was filtered off. The filtrate was evaporated to a minimum and dried at 50° C. under vacuum overnight to yield the title compound (D35) as a white powder (1.21 g). MS electrospray (+ion) 310 (MH⁺).

Description 36

2-Chloro-4-[(1-cyclobutyl-4-piperidinyl)oxy]benzoyl chloride hydrochloride (D36)

2-Chloro-4-[(1-cyclobutyl-4-piperidinyl)oxy]benzoic acid hydrochloride (D35) (0.20 g) was dissolved in thionyl chloride (10 ml) and heated under reflux for 1.5 h. The thionyl chloride was removed by evaporation and the residue evaporated from DCM (3×10 ml) to give the title compound (D36) (0.21 g).

EXAMPLE 1

N-[4-(3-Piperidin-1-ylpropoxy)benzoyl]indoline hydrochloride (E1)

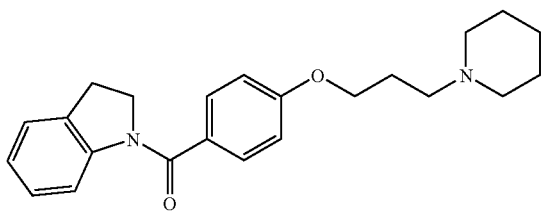

A solution of 4-(3-piperidin-1-ylpropoxy)benzoic acid hydrochloride (D2) (150 mg) in thionyl chloride (4 ml) was refluxed for 1 h, cooled to rt and evaporated. The acid chloride was re-evaporated from DCM (2×3 ml). The residue was redissolved in DCM (5 ml) and triethylamine (0.21 ml) and added to a stirred solution of indoline (54 mg) in DCM (2 ml) at rt. The mixture was stirred for 1 h, washed with saturated sodium hydrogen carbonate solution (5 ml), water (3×5 ml), dried (MgSO₄) and evaporated. The residue was chromatographed (silica gel, step gradient 4-8% MeOH in DCM). Fractions containing the required product were treated with excess hydrogen chloride (4M solution in dioxan) and then concentrated to yield the title compound (E1) (126 mg). MS electrospray (+ion) 365 (MH⁺). ¹H NMR δ (DMSO-d6): 10.21 (1H, s), 6.95-7.81 (8H, m), 4.14 (2H, t, J=6 Hz), 4.04 (2H, t, J=8 Hz), 2.80-3.00 (6H, m), 2.88 (2H, m), 2.20 (2H, m), 130-1.85 (6H, m).

EXAMPLE 2

(Method A)

N-[4-(3-Piperidin-1-ylpropoxy)benzoyl]isoindoline hydrochloride (E2)

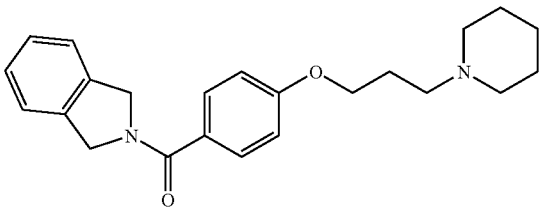

4-(3-Piperidin-1-ylpropoxy)benzoic acid hydrochloride (D2) (150 mg) was converted to the title compound (E2) by reaction with isoindoline (54 mg) using the method described in Example 1 (E1) (yield=198 mg). MS electrospray (+ion) 365 (MH$^+$). $^1$H NMR δ (DMSO-d6): 10.33 (1H, s), 7.62 (2H, d, J=8.8 Hz), 7.02 (2H, d, J=8.8 Hz), 7.31 (4H, m), 4.86 (2H, s), 4.82 (2H, s), 4.13 (2H, t, J=6.5 Hz), 2.80-3.52 (6H, m), 2.21 (2H, m), 1.30-1.85 (6H, m).

EXAMPLE 2

(Method B)

N-[4-(3-Piperidin-1-ylpropoxy)benzoyl]isoindoline hydrochloride (E2)

A stirred suspension of 4-(3-piperidin-1-ylpropoxy)benzoic acid hydrochloride (D2 (Method B); 25 g) in DCM (250 ml) at rt was treated with oxalyl chloride (10.92 ml) and 10% DMF in DCM (1 drop). After 2 h the solution was evaporate.d and then re-evaporated from DCM (100 ml) and toluene (100 ml). The acid chloride was redissolved in DCM (400 ml) and treated with isoindoline hydrochloride (12.8 g). The stirred mixture was cooled in ice and triethylamine (46.4 ml) was added over 20 min. The mixture was allowed to gain rt and stirred for 1 h. The solution was washed with saturated sodium hydrogen carbonate solution (2×200 ml), water (2×200 ml), brine (200 ml), dried (MgSO$_4$) and evaporated. The residue was chromatographed on a silica gel flash column [step gradient 5-9% MeOH (containing 10% 0.880 ammonia solution) in DCM]. Fractions containing the required product were evaporated and then re-evaporated from EtOH to give a solid (27.5 g) which was redissolved in DCM (300 ml), treated with 4M HCl in dioxan (28.3 ml) and then evaporated. The resulting solid was crystallised from EtOH/diethyl ether to give 2 crops (28.5 g). This material was recrystallised from MeOH/diethyl ether to give the title compound (E2) (26.4 g).

EXAMPLE 3

N-[4-(3-Piperidin-1-ylpropoxy)benzoyl]-3,4-dihydro-1H-isoquinoline hydrochloride (E3)

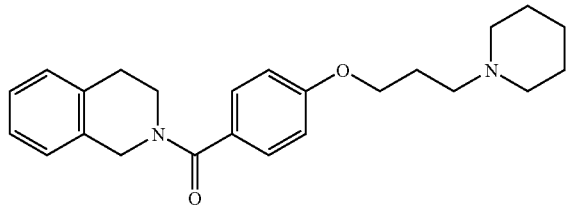

4-(3-Piperidin-1-ylpropoxy)benzoic acid hydrochloride (D2) (299 mg) was converted to the title compound (E3) by reaction with 1,2,3,4-tetrahydroisoquinoline (133 mg) using the method described in Example 1 (E1) (yield=376 mg). MS electrospray (+ion) 379 (MH$^+$). $^1$H NMR δ (DMSO-d6): 9.89 (1H, s), 7.00-7.45 (8H, m), 4.69 (2H, s), 4.11 (2H, t, J=6 Hz), 3.7 (2H, m), 3.46 (2H, m), 3.18 (2H, m), 2.89 (4H, m), 2.18 (2H, m), 1.30-1.87 (6H, m).

EXAMPLE 4

N-[4-(3-Piperidin-1-ylpropoxy)benzoyl]-5-bromoindoline hydrochloride (E4)

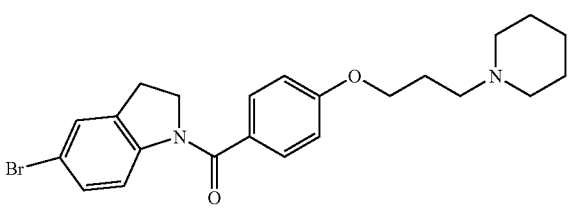

4-(3-Piperidin-1-ylpropoxy)benzoic acid hydrochloride (D2) (299 mg) was converted to the title compound (E4) by reaction with 5-bromoindoline (198 mg) using the method described in Example 1 (E1) (yield=372 mg). MS electrospray (+ion) 443, 445 (MH$^+$). $^1$H NMR δ (DMSO-d6): 10.05 (1H, s), 7.01-7.82 (7H, m), 4.11 (2H, t, J=6 Hz), 4.06 (2H, m), 3.46 (2H, m), 3.19 (2H, m), 3.09 (2H, m), 2.21 (2H, m), 1.30-1.87 (6H, m).

EXAMPLE 5

N-[4-(3-Piperidin-1-ylpropoxy)benzoyl]indole hydrochloride (E5)

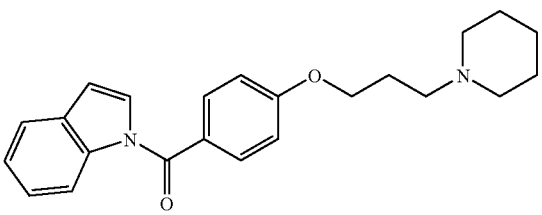

A solution of 4-(3-piperidin-1-ylpropoxy)benzoic acid hydrochloride (D2) (150 mg) in thionyl chloride (4 ml) was refluxed for 1 h, cooled to rt and evaporated. The acid chloride was re-evaporated from DCM (2×3 ml). The residue was redissolved in DMF (3 ml) and added to an ice-cold stirred solution of indole (59 mg) and sodium hydride (40 mg of a 60% dispersion in oil)in DMF (2 ml). The mixture was stirred for 1 h then 2 h at rt. Methanol (2 ml) was added and the mixture evaporated. The residue was chromatographed (silica gel, step gradient 4-8% MeOH in DCM). Fractions containing the required product were treated with excess hydrogen chloride (4M solution in dioxan) and then concentrated to yield the title compound (E5) (72 mg). MS electrospray (+ion) 363 (MH$^+$). $^1$H NMR δ(DMSO-d6): 10.30 (1H, s), 6.75-8.22 (10H, m), 4.20 (2H, t, J=6 Hz), 2.80-3.55 (6H, m), 2.25 (2H, m), 1.25-1.91 (6H, m).

EXAMPLE 6

5-Fluoro-2-methyl-N-[4-(3-piperidin-1-ylpropoxy)benzoyl]-indole hydrochloride (E6)

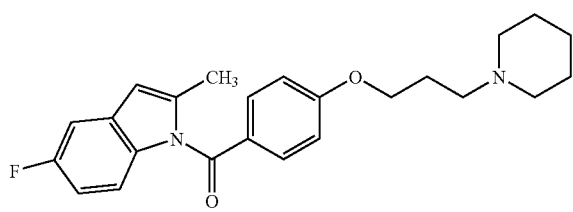

The title compound (E6) was prepared from 4-(3-piperidin-1-ylpropoxy)benzoic acid hydrochloride (D2) and 5-fluoro-2-methyl-indole using the method described in Example 5 (E5).

EXAMPLE 7

5-Methoxy-2-methyl-N-[4-(3-piperidin-1-ylpropoxy)benzoyl]-indole hydrochloride (E7)

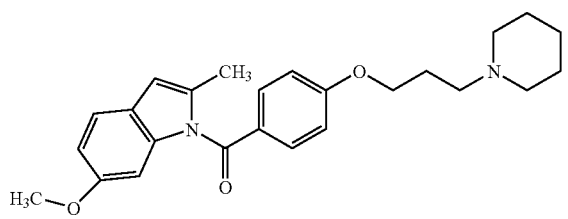

The title compound (E7) was prepared from 4-(3-piperidin-1-ylpropoxy)benzoic acid hydrochloride (D2) and 5-methoxy-2-methyl-indole using the method described in Example 5 (E5).

EXAMPLES 8-10

(E8-10)

Examples 8-10 were prepared from 4-(3-piperidin-1-ylpropoxy)benzoic acid hydrochloride (D2) and the appropriate amine using the method outlined in Example 1 (E1) and displayed $^1$H NMR and mass spectral data that were consistent with structure.

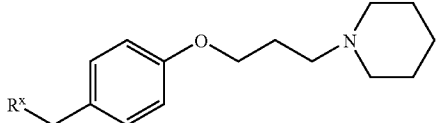

| Example No | R$^x$ | Mass Spectrum (ES$^+$) |
|---|---|---|
| E8 | 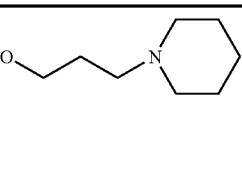 | 383 [M + H]$^+$ |
| E9 | (1-methylindoline) | 379 [M + H]$^+$ |
| E10 | (1-methyl-1,2,3,4-tetrahydroquinoline) | 379 [M + H]$^+$ |

EXAMPLE 11

N-[4-(3-Piperidin-1-ylpropoxy)-benzoyl]-5-fluoroisoindoline hydrochloride (E11)

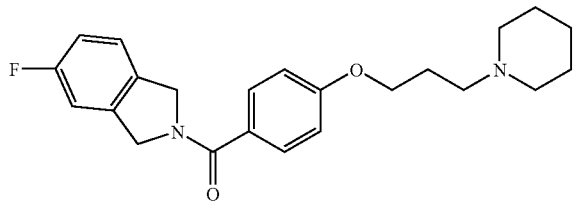

A stirred mixture of 5-fluoroisoindoline hydrochloride (D8) (183 mg) and diethylaminoethylpolystyrene (626 mg, 3.2 mmol/g) in DCM (10 ml) at rt was treated with 4-(3-piperidin-1-ylpropoxy)-benzoyl chloride hydrochloride (223 mg) (D3). After 1 h the reaction mixture was chromatographed directly [silica gel, step gradient 0-10% MeOH (containing 10% 0.880 ammonia solution) in DCM)]. Fractions containing the required product were evaporated, redissolved in DCM, treated with excess hydrogen chloride (4M solution in dioxan) and then evaporated. The residue was triturated with acetone, filtered, washed with acetone and dried to yield the title compound (E11) (80 mg). MS electrospray (+ion) 383 (MH$^+$). $^1$H NMR δ (DMSO-d6): 10.21 (1H, s), 7.61 (2H, d, J=8.8 Hz), 7.05-7.50 (3H, m), 7.01 (2H, d, J=8.8 Hz), 4.81 (4H, m), 4.13. (2H, t, J=6 Hz), 3.46 (2H, m), 3.15 (2H, m), 2.88 (2H, m), 2.21 (2H, m), 1.28-1.92 (6H, m).

EXAMPLE 12

N-[4-(3-Piperidin-1-ylpropoxy)-benzoyl]-5-nitroisoindoline hydrochloride (E12)

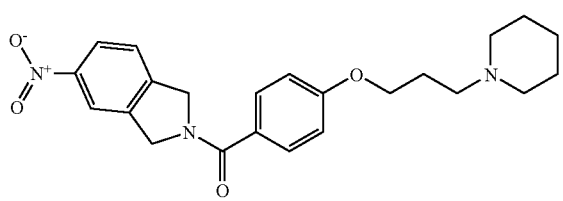

An ice cold stirred mixture of 5-nitroisoindoline (2.27 g) (Fraenkel, Chem Ber 1900, 33, 2811) and 4-(3-piperidin-1-ylpropoxy)-benzoyl chloride hydrochloride (3.35 g) (D3) in DCM (50 ml) was treated dropwise with triethylamine (5.56 ml). The reaction mixture was allowed to gain rt, stirred for 1 h then washed with saturated sodium hydrogen carbonate solution (50 ml), water (3×50 ml), brine (50 ml), dried (MgSO$_4$) and evaporated. Chromatography [silica gel, step gradient 0-10% MeOH (containing 10% 0.880 ammonia solution) in DCM] afforded the free base (2.92 g). A sample (47 mg) in DCM (2 ml) was treated with excess 4M HCl in dioxan and evaporated to give the title compound (E12) (51 mg). MS electrospray (+ion) 410 (MH$^+$). $^1$H NMR δ (DMSO-d6): 10.20 (1H, s), 8.25 (2H, m), 7.62 (3H, m), 7.03 (2H, d, J=8.8 Hz), 4.95 (4H, m), 4.14. (2H, t, J=6 Hz), 3.45 (2H, m), 3.20 (2H, m), 2.90 (2H, m), 2.20 (2H, m), 1.28-1.92 (6H, m).

EXAMPLE 13

N-[4-(3-Piperidin-1-ylpropoxy)-benzoyl]-5-aminoisoindoline hydrochloride (E13)

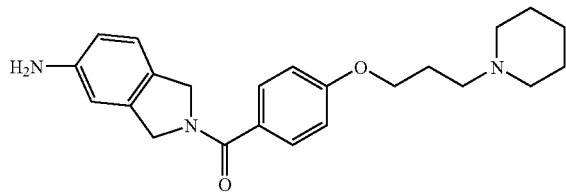

A stirred solution of N-[4-(3-piperidin-1-ylpropoxy)-benzoyl]-5-nitroisoindoline (E12) (0.5 g) in THF (50 ml) was treated with titanium (III) chloride (5.63 ml of a 30% w/v solution in hydrochloric acid). After 3 h EDTA (2.85 g) and water (100 ml) were added and the mixture stirred for 15 min. The mixture was made basic with potassium carbonate and extracted with DCM (2×75 ml). The combined extracts were dried (MgSO$_4$) and evaporated. Chromatography [silica gel, step gradient 0-10% MeOH (containing 10% 0.880 ammonia solution) in DCM] afforded the free base (430 mg). A sample (25 mg) in DCM (2 ml) was treated with excess 4M HCl in dioxan and evaporated to give the title compound (E13) (26 mg). MS electrospray (+ion) 380 (MH$^+$). $^1$H NMR δ (DMSO-d6): 10.41 (1H, s), 9.80 (2H, bs), 7.61 (2H, d, J=8.5 Hz), 7.09-7.51 (3H, m), 7.03 (2H, d, J=8.5 Hz), 4.85 (4H, m), 4.10. (2H, t, J=6 Hz), 3.45 (2H, m), 3.19 (2H, m), 2.91 (2H, m), 2.21 (2H, m), 1.28-1.95 (6H, m).

EXAMPLE 14

N-[4-(3-Piperidin-1-ylpropoxy)-benzoyl]-5-(1-succinimido)-isoindoline hydrochloride (E14)

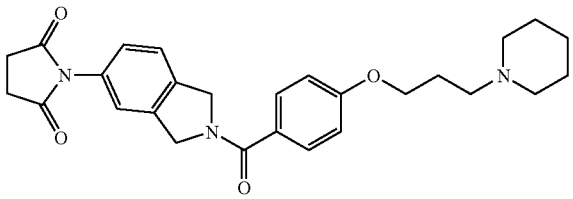

A stirred mixture of succinic anhydride (79 mg) and N-[4-(3-piperidin-1-ylpropoxy)-benzoyl ]-5-aminoisoindoline hydrochloride (E13) (150 mg) were fused at 150° C. for 2 h. The mixture was cooled to rt and partitioned between EtOAc (10 ml) and saturated sodium hydrogen carbonate solution (10 ml). The organic layer was washed with water (2×10 ml), brine (10 ml), dried (MgSO$_4$) and evaporated. The residue was dissolved in DCM, treated with excess 4M HCl in dioxan and evaporated. Crystallisation from EtOH/diethyl ether gave the title compound (E14) (90 mg). MS electrospray (+ion) 462 (MH$^+$). $^1$H NMR δ (DMSO-d6): 10.15 (1H, s), 7.63 (2H, d, J=8.5 Hz), 7.08-7.54 (3H, m), 7.02 (2H, d, J=8.5 Hz), 4.87 (4H, m), 4.13. (2H, t, J=6 Hz), 3.09-3.52 (8H, m), 2.91 (2H, m), 2.21 (2H, m), 1.30-1.88 (6H, m).

EXAMPLE 15

N-[4-(3-Piperidin-1-ylpropoxy)-benzoyl]-5-(2-oxopyrrolidin-1-yl)-isoindoline hydrochloride (E15)

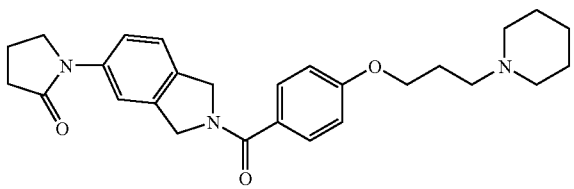

A stirred mixture of diethylaminomethyl polystyrene (247 mg, 3.2 mmol/g) and N-[4-(3-piperidin-1-ylpropoxy)-benzoyl]-5-aminoisoindoline hydrochloride (E13) (150 mg) in DCM (5 ml) at rt was treated with 4-bromobutanoyl chloride (0.05 ml) for 30 mins. The mixture was filtered and evaporated. The residue was redissolved in DMF (5 ml) and treated with sodium hydride (18 mg of a 60% suspension in mineral oil) and stirred for 2 h. A further portion of sodium hydride (18 mg) was added and the mixture stirred for 1 h. The reaction was partitioned between EtOAc (10 ml) and saturated sodium hydrogen carbonate solution (10 ml). The organic layer was washed with water (2×10 ml), brine (10 ml), dried (MgSO$_4$) and evaporated. After chromatography [silica gel, step gradient 0-10% MeOH (containing 10% 0.880 ammonia solution) in DCM] fractions containing the required product were evaporated, then redissolved in DCM, treated with excess 4M HCl in dioxan and evaporated. Crystallisation from EtOH/diethyl ether afforded the title compound (E15) (77 mg). MS electrospray (+ion) 448 (MH$^+$). $^1$H NMR δ (DMSO-d6): 10.15 (1H, s), 7.60 (4H, m), 7.34 (1H, m), 7.0 (2H, d, J=8.5 Hz), 4.80 (4H, m), 4.13. (2H, t, J=6 Hz), 3.80 (2H, m), 3.05-3.58 (6H, m), 2.91 (2H, m), 2.21 (2H, m), 2.06 (2H, m), 1.28-1.90 (6H, m).

EXAMPLE 16

N-[4-(3-Piperidin-1-ylpropoxy)-2-trifluoromethylbenzoyl]isoindoline hydrochloride (E16)

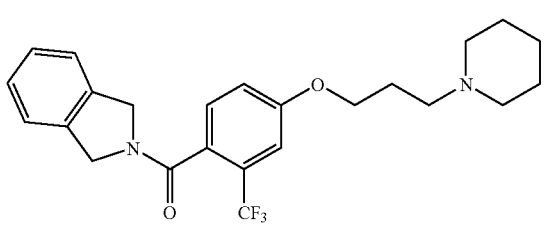

A solution of 4-(3-piperidin-1-yl-propoxy)-2-trifluoromethyl-benzoyl chloride (D6) (150 mg) in DCM (10 ml) was added to isoindoline (0.046 ml) and diethylaminomethyl polystyrene (0.60 g; 3.2 mmol/g). The mixture was stirred for 16 h, then loaded directly onto a silica column and eluted with 0-10% MeOH (containing 10% 0.880 ammonia solution) in DCM. The isolated free base was dissolved in DCM (5 ml) and treated with 4N HCl/dioxane solution (1 ml) with stirring for 10 min. The mixture was concentrated, and the residue co-evaporated with toluene (3×10 ml) and then dried at 50° C. under high vacuum for 16 h to yield the title compound (E16) as a beige solid (0.094 g). MS electrospray (+ion) 433 (MH$^+$). $^1$H NMR δ (DMSO-d6): 9.96 (1H, s), 7.63 (1H, d, J=8.36 Hz), 7.46-7.23 (6H, m), 4.82 (2H, s), 4.47 (2H, s), 4.20 (2H, t, J=5.88 Hz), 3.47 (2H, m), 3.19 (2H, m), 2.87 (2H, m), 2.20 (2H, m), 1.80-1.38 (6H, m).

EXAMPLE 17

N-[4-(3-Piperidin-1-ylpropoxy)benzoyl]-6-cyano-1,2,3,4-tetrahydroisoquinoline hydrochloride (E17)

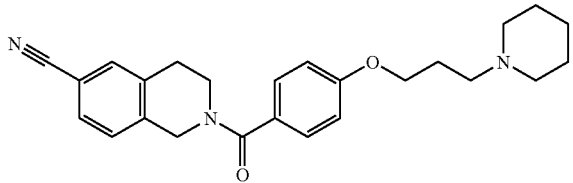

The title compound was prepared from 4-(3-piperidin-1-ylpropoxy)benzoyl chloride hydrochloride (D3) (0.20 g) and 6-cyano-1,2,3,4-tetrahydroisoquinoline hydrochloride (WO98/50363) (0.15 g) using the procedure described for Example 1 and isolated as a white solid (0.13 g). MS electrospray (+ion) 404 (MH$^+$). $^1$H NMR δ (DMSO-d6): 10.20 (1H, s), 7.69 (1H, s), 7.65 (1H, d, J=7.5 Hz), 7.45 (3H, m), 7.02 (2H, d, J=8.6 Hz), 4.76 (1H, s), 4.11 (1H, t, J=5.9), 3.68 (2H, m), 3.44 (2H, m), 3.17 (2H, m), 2.90 (4H, m), 2.19 (2H, m), 1.78-1.37 (6H, m).

EXAMPLE 18

N-[4-(3-Piperidin-1-ylpropoxy)benzoyl]-7-cyano-1,2,3,4-tetrahydroisoquinoline hydrochloride (E18)

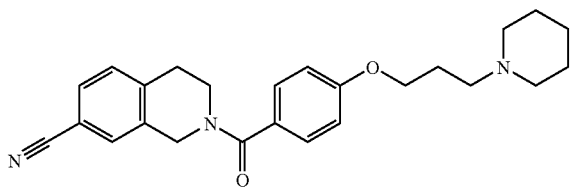

A solution of 4-(3-piperidin-1-ylpropoxy)benzoyl chloride hydrochloride (D3) (0.14 g) in DCM (10 ml) was added to 7-cyano-1,2,3,4-tetrahydroisoquinoline (WO98/50364) (0.08 g) and diethylaminomethyl polystyrene (0.6 g, 3.2 mmol/g). The mixture was stirred for 16 h then loaded directly onto a silica column and eluted with 0-10% MeOH (containing 10% 0.880 ammonia solution) in DCM. The isolated free base was dissolved in DCM (5 ml) and treated with 4N HCl/dioxane solution (1 ml) with stirring for 10 min. The mixture was concentrated and the residue co-evaporated with toluene (3×10 ml) then crystallised from ethanol/diethyl ether, and dried at 80° C. under high vacuum for 16 h to yield the title compound (E18) as a beige solid (0.03 g). MS electrospray (+ion) 404 (MH$^+$). $^1$H NMR δ (DMSO-d6): 9.91 (1H, s), 7.85 (1H, m), 7.65 (1H, d, J=7.9 Hz), 7.42 (3H, m), 7.02 (2H, d, J=8.6), 4.73 (2H, s), 4.11 (2H, t, J=5.9 Hz), 3.68 (2H, m), 3.44 (2H, m), 3.17 (2H, m), 2.93 (4H, m), 2.20 (2H, m), 1.91-1.41 (6H, m).

EXAMPLE 19

N-[4-(3-Piperidin-1-ylpropoxy)benzoyl]-2,3,4,5-tetrahydro-1H-3-benzazepine hydrochloride (E19)

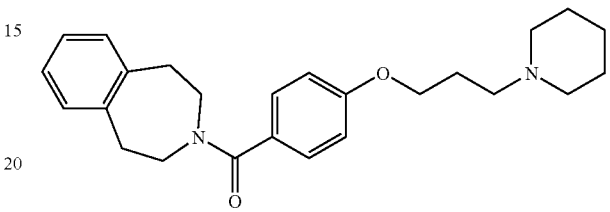

The title compound was prepared from 4-(3-piperidin-1-ylpropoxy)benzoyl chloride hydrochloride (D3) (0.20 g) and 2,3,4,5-tetrahydro-1H-3-benzazepine (WO00/21951) (0.89 g) using the procedure described for Example 1 and isolated as a white solid (0.16 g). MS electrospray (+ion) 393 (MH$^+$). $^1$H NMR δ (DMSO-d6): 9.68 (1H, s), 7.34 (2H, d, J=6.8 Hz), 7.14 (4H, m), 7.00 (2H, d, J=6.8 Hz), 4.10 (2H, t, J=5.9 Hz), 3.81-3.45 (6H, m), 3.17 (2H, m), 2.90 (6H, m), 2.17 (2H, m), 1.83-1.37 (6H, m).

EXAMPLE 20

N-[4-(3-Piperidin-1-ylpropoxy)benzoyl]-7-methylsulfonyl-2,3,4,5-tetrahydro-1H-3-benzazepine hydrochloride (E20)

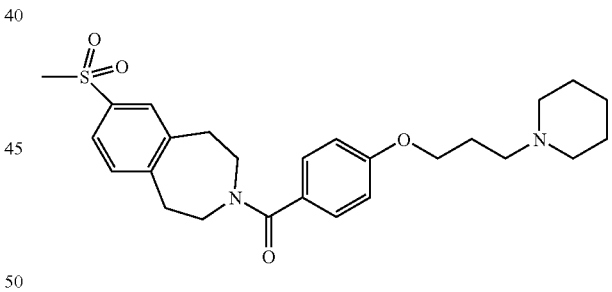

The title compound was prepared from 4-(3-piperidin-1-ylpropoxy)benzoyl chloride hydrochloride (D3) (0.20 g) and 7-methanesulfonyl-2,3,4,5-tetrahydro-1H-3-benzazepine (WO00/21951) (0.17 g) using the procedure described for Example 1 and isolated as a white solid (0.24 g). MS electrospray (+ion) 471 (MH$^+$). $^1$H NMR δ (DMSO-d6): 9.83 (1H, s), 7.71 (2H, m), 7.44 (1H, s), 7.35 (2H, d, J=8.5 Hz ), 7.01 (2H, d, J=8.6 Hz), 4.11 (2H, t, J=5.9 Hz), 3.71-3.45 (6H, m), 3.18 (6H, m), 3.05 (3H, s) 2.87 (2H, m), 2.20 (2H, m), 1.83-1.37 (6H, m).

EXAMPLES 21-49

(E21-E49)

Examples 21-49 were prepared from 4-(3-piperidin-1-ylpropoxy)benzoyl chloride hydrochloride (D3) and the appropriate amine using the method outlined in Example 11 (E11) and displayed ¹H NMR and mass spectral data that were consistent with structure.
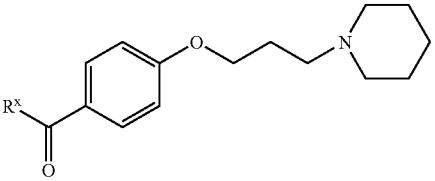
| Example No | R$^x$ | Mass Spectrum (ES⁺) |
|---|---|---|
| E21 | 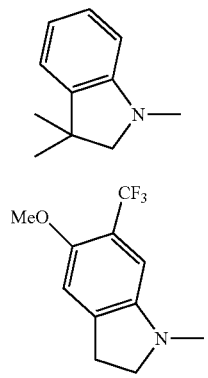 | [M + H]⁺ 393 |
| E22 | 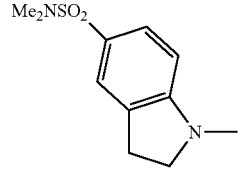 | [M + H]⁺ 463 |
| E23 | 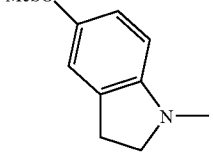 | [M + H]⁺ 472 |
| E24 | 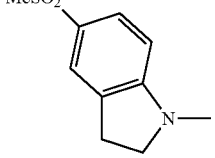 | [M + H]⁺ 427 |
| E25 | 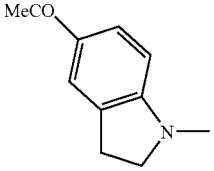 | [M + H]⁺ 443 |
| E26 | 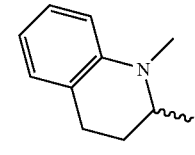 | [M + H]⁺ 407 |
| E27 | 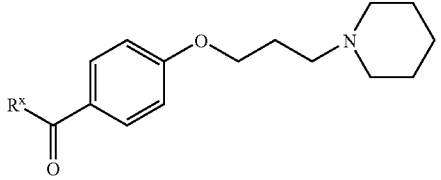 | [M + H]⁺ 393 |
-continued
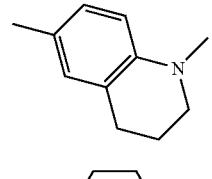
| Example No | R$^x$ | Mass Spectrum (ES⁺) |
|---|---|---|
| E28 | 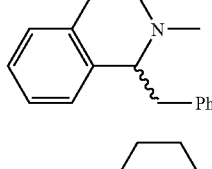 | [M + H]⁺ 393 |
| E29 | 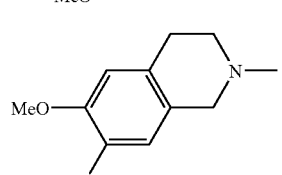 | [M + H]⁺ 469 |
| E30 | 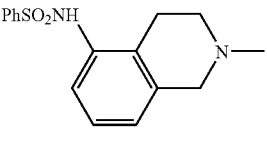 | [M + H]⁺ 515 |
| E31 | 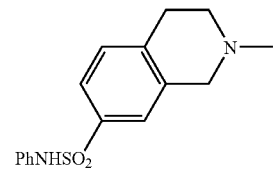 | [M + H]⁺ 439 |
| E32 | 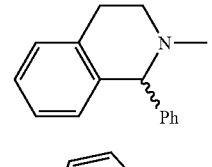 | [M + H]⁺ 534 |
| E33 | 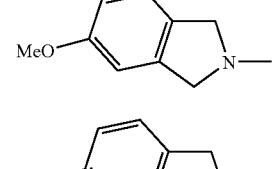 | [M + H]⁺ 534 |
| E34 | 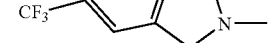 | [M + H]⁺ 455 |
| E35 | | [M + H]⁺ 395 |
| E36 | | [M + H]⁺ 433 |

-continued
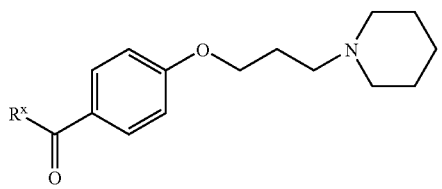
| Example No | Rˣ | Mass Spectrum (ES⁺) |
|---|---|---|
| E37 | 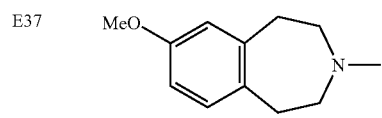 | [M + H]⁺ 424 |
| E38 | 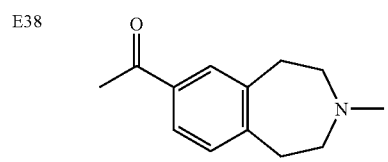 | [M + H]⁺ 434 |
| E39 | 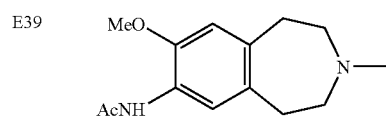 | [M + H]⁺ 480 |
| E40 | 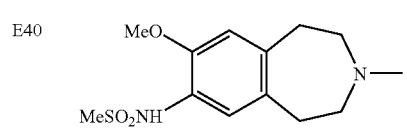 | [M + H]⁺ 516 |
| E41 | 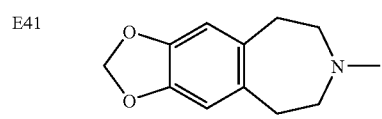 | [M + H]⁺ 437 |
| E42 | 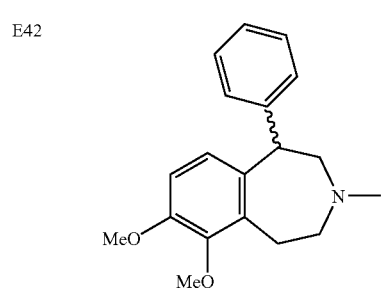 | [M + H]⁺ 530 |
| E43 | 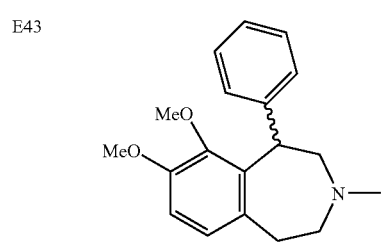 | [M + H]⁺ 530 |
-continued
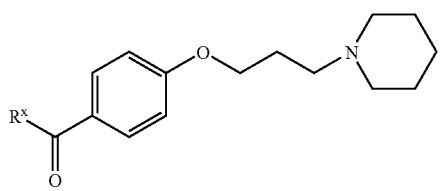
| Example No | Rˣ | Mass Spectrum (ES⁺) |
|---|---|---|
| E44 | 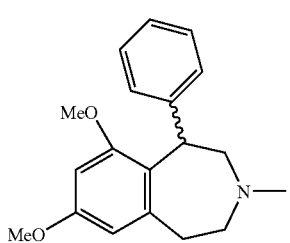 | [M + H]⁺ 530 |
| E45 | 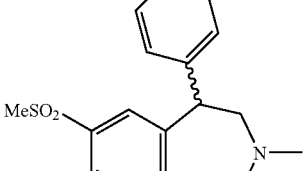 | [M + H]⁺ 564 |
| E46 | 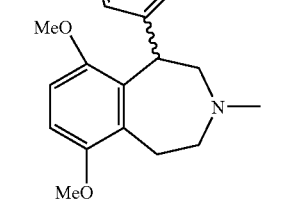 | [M + H]⁺ 559 |
| E47 | 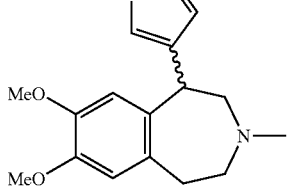 | [M + H]⁺ 536 |
| E48 | 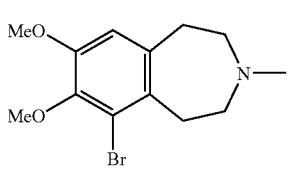 | [M + H]⁺ 532 |

-continued

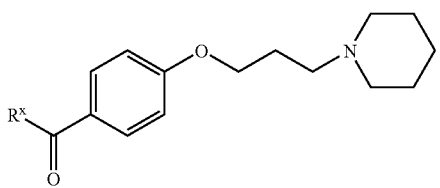

| Example No | R<sup>x</sup> | Mass Spectrum (ES+) |
|---|---|---|
| E49 | iPrSO$_2$ | [M + H]$^+$ 669 |
| | MeO-, MeO-, Cl-substituted benzazepine attached to phenyl | |

EXAMPLES 50-53

(E50-53)

Examples 50-53 were prepared from 4-(3-piperidin-1-yl-propoxy)benzoyl chloride hydrochloride (D3) and the appropriate amine using the method outlined in Example 11 (E11) and displayed $^1$H NMR and mass spectral data that were consistent with structure.

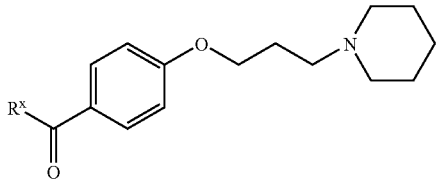

| Example No | R$^x$ | Mass Spectrum (ES+) |
|---|---|---|
| E50 | 7-F tetrahydroisoquinoline | [M + H]$^+$ 397 |
| E51 | 6-Cl tetrahydroisoquinoline | [M + H]$^+$ 413, 415 |

-continued

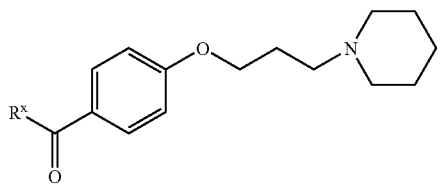

| Example No | R$^x$ | Mass Spectrum (ES+) |
|---|---|---|
| E52 | 7,8-diCl tetrahydroisoquinoline | [M + H]$^+$ 447, 449, 451 |
| E53 | 8-Cl tetrahydroisoquinoline | [M + H]$^+$ 413, 415 |

EXAMPLE 54

N-[4-(3-Piperidin-1-ylpropoxy)benzoyl]-7-cyano-2,3,4,5-tetrahydro-1H-3-benzazepine hydrochloride
(E54)

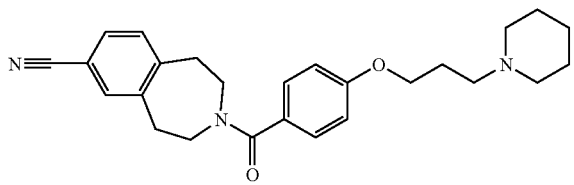

A stirred suspension of 4-(3-piperidin-1-ylpropoxy)benzoic acid hydrochloride (D2) (150 mg) in DCM (5 ml) at rt was treated with oxalyl chloride (0.1 ml) and 10% DMF in DCM (1 drop). After 1 h the solution was evaporated and then re-evaporated from DCM (2×5 ml). The acid chloride was redissolved in DCM (10 ml) and treated with 7-cyano-2,3,4,5-tetrahydro-1H-3-benzazepine (104 mg) and diethylaminomethyl polystyrene (3.2 mmol/g, 626 mg). After stirring overnight the mixture was loaded directly on to a silica gel flash column [step gradient 4-10% MeOH (containing 10% 0.880 ammonia solution) in DCM]. The required fractions were evaporated, then redissolved in DCM and treated with excess 4M HCl in dioxan. The title compound (E54) (137 mg) was obtained by crystallisation from acetone (137 mg). MS electrospray (+ion) 418 (MH$^+$). $^1$H NMR δ (DMSO-d6): 10.34 (1H, m), 7.65 (2H, m), 7.35 (3H, m), 6.99 (2H, d, J=8.8 Hz), 4.11 (2H, t, J=6 Hz), 2.70-3.85 (14H, m), 2.19 (2H, m), 1.79 (5H, m), 1.41 (1H, m).

EXAMPLE 55

N-[4-(3-Piperidin-1-ylpropoxy)benzoyl]-4-fluoroisoindoline hydrochloride (E55)

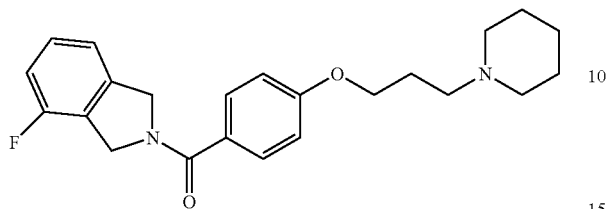

A mixture of pentachlorophenyl 4-(3-piperdin-1-ylpropoxy)benzoate (D10) (500 mg) and N-benzyl-4-fluoroisoindoline (D9) (200 mg) in IPA (10 ml) at rt was treated with poly(methylhydrosiloxane) (0.16 ml) and palladium hydroxide on carbon (30 mg, 20% Pd) and stirred overnight. The mixture was filtered and evaporated. The residue was redissolved in EtOAc (20 ml), washed with saturated sodium hydrogen carbonate solution (10 ml), water (2×10 ml), brine (10 ml), dried (MgSO$_4$) and evaporated. The residue was chromatographed on a silica gel flash column [step gradient 2-8% MeOH (containing 10% 0.880 ammonia solution) in DCM]. The required fractions were evaporated, then redissolved in DCM and treated with excess 4M HCl in dioxan. The title compound (E55) (65 mg) was obtained by crystallisation from acetone. MS electrospray (+ion) 383 (MH$^+$). $^1$H NMR δ (DMSO-d6): 10.15 (1H, m), 7.09-7.65 (7H, m), 4.89 (4H, m), 4.13 (2H, t, J=6 Hz), 3.46 (2H, m), 3.16 (2H, m), 2.90 (2H, m), 2.22 (2H, m), 1.79 (5H, m), 1.42 (1H, m).

EXAMPLE 56

N-[4-(3-Piperidin-1-ylpropoxy)benzoyl]-5-cyanoisoindoline hydrochloride (E56)

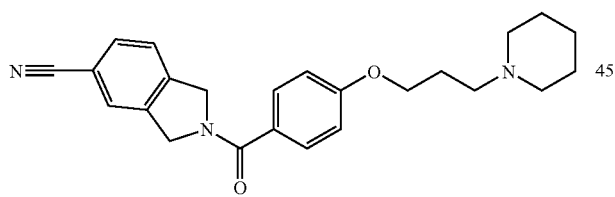

A stirred suspension of 4-(3-piperdin-1-ylpropoxy)benzoic acid hydrochloride (D2) (150 mg) in DCM (5 ml) at rt was treated with oxalyl chloride (0.1 ml) and 10% DMF in DCM (1 drop). After 1 h the solution was evaporated and then reevaporated from DCM (2×5 ml). The acid chloride was redissolved in DCM (10 ml) and treated with 5-cyanoisoindoline trifluoroacetate (D16) (140 mg) and triethylamine (0.3 ml) then stirred overnight and evaporated. The residue was redissolved in EtOAc (20 ml), washed with saturated sodium hydrogen carbonate solution (10 ml), water (2×10 ml), brine (10 ml), dried (MgSO$_4$) and evaporated. The residue was chromatographed on a silica gel flash column [step gradient 2-8% MeOH (containing 10% 0.880 ammonia solution) in DCM]. The required fractions were evaporated, then redissolved in DCM and treated with excess 4M HCl in dioxan. The title compound (E56) (60 mg) was obtained by crystallisation from acetone. MS electrospray (+ion) 390 (MH$^+$). $^1$H NMR δ (DMSO-d6): 10.22 (1H, m), 7.48-7.90 (5H, m), 7.02 (2H, d, J=8.8 Hz), 4.89 (4H, m), 4.13 (2H, t, J=6 Hz), 3.45 (2H, m), 3.17 (2H, m), 2.88 (2H, m), 2.22 (2H, m), 1.79 (5H, m), 1.40 (1H, m).

EXAMPLE 57

N-[4-(3-Piperidin-1-ylpropoxy)benzoyl]-5-[(pyrrolidin-1-yl)carbonyl]isoindoline hydrochloride (E57)

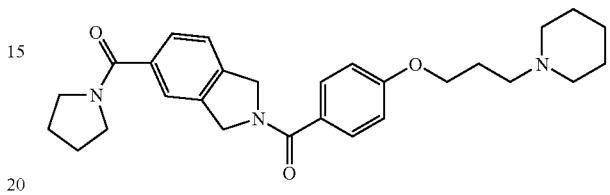

A stirred suspension of 4-(3-piperidin-1-ylpropoxy)benzoic acid hydrochloride (D2) (101 mg) in DCM (5 ml) at rt was treated with oxalyl chloride (0.06 ml) and 10% DMF in DCM (1 drop). After 1 h the solution was evaporated and then re-evaporated from DCM (2×5 ml). The acid chloride was redissolved in DCM (10 ml) and treated with 5-[(pyrrolidin-1yl)carbonyl]isoindoline hydrochloride (D18) (85 mg) and diethylaminomethyl polystyrene (3.2 mmol/g, 421 mg). After stirring overnight the mixture was loaded directly on to a silica gel flash column [step gradient 6-9% MeOH (containing 10% 0.880 ammonia solution) in DCM]. The required fractions were evaporated, then redissolved in DCM and treated with excess 4M HCl in dioxan. The title compound (E57) (137 mg) was obtained by crystallisation from acetone. MS electrospray (+ion) 390 (MH$^+$). $^1$H NMR δ (DMSO-d6): 10.09 (1H, m), 7.00-7.64 (7H, m), 4.86 (4H, m), 4.13 (2H, t, J=6 Hz), 3.37 (4H, m), 3.17 (2H, m), 2.89 (2H, m), 2.22 (2H, m), 1.82 (11H, m), 1.41 (1H, m).

EXAMPLE 58

N-[4-(3-Piperidin-1-ylpropoxy)benzoyl]-5-[(morpholin-4-yl)carbonyl]isoindoline hydrochloride (E58)

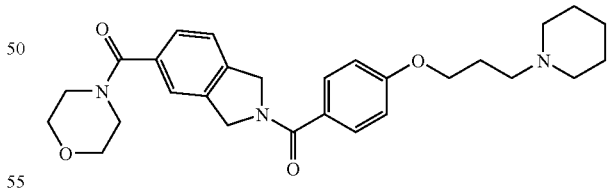

A stirred suspension of 4-(3-piperidin-1-ylpropoxy)benzoic acid hydrochloride (D2) (262 mg) in DCM (5 ml) at rt was treated with oxalyl chloride (0.15 ml) and 10% DMF in DCM (1 drop). After 1 h the solution was evaporated and then re-evaporated from DCM (2×5 ml). The acid chloride was redissolved in DCM (10 ml) and treated with 5-[(morpholin-4-yl)carbonyl]isoindoline trifluoroacetate (D20) (305 mg) and triethylamine (0.61 ml) stirred overnight and evaporated. The residue was redissolved in EtOAc (20 ml), washed with saturated sodium hydrogen carbonate solution (10 ml), water (2×10 ml), brine (10 ml), dried (MgSO$_4$) and evaporated. The residue was chromatographed on a silica gel flash column [step gradient 6-9% MeOH (containing 10% 0.880 ammonia solution) in DCM]. The required fractions were evaporated, then redissolved in DCM and treated with excess 4M HCl in dioxan. The title compound (E58) (170 mg) was obtained by crystallisation from EtOH/diethyl ether. MS electrospray (+ion) 478 (MH$^+$). $^1$H NMR δ (DMSO-d6): 10.32 (1H, m), 7.62 (2H, d J=8.8 Hz), 7.33-7.49 (5H, m), 7.02 (2H, d, J=8.8 Hz), 4.86 (4H, m), 4.13 (2H, t, J=6 Hz), 3.45 (8H, m), 3.17 (2H, m), 2.92 (2H, m), 2.22 (2H, m), 1.80 (5H, m), 1.41 (1H, m).

EXAMPLE 59

N-{4-[(1-Cyclobutyl-4-piperidinyl)oxy]benzoyl}isoindoline hydrochloride (E59)

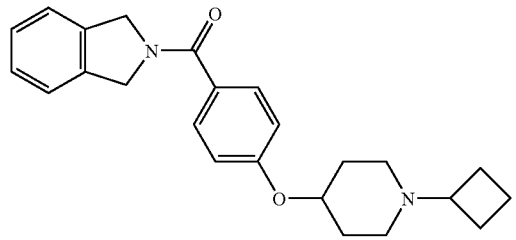

A stirred mixture of 4-[(1-cyclobutyl-4-piperidinyl)oxy]benzoyl chloride hydrochloride (D25) (0.25 g) and diethylaminomethyl polystyrene (3.2 mmol/g, 1.13 g) in DCM (10 ml) at rt was treated with isoindoline (0.098 g) and stirred for 16 h. The reaction mixture was chromatographed directly [silica gel, step gradient 0-10% MeOH (containing 10% 0.880 ammonia solution) in DCM)]. Fractions containing the required product were evaporated, redissolved in DCM, treated with excess hydrogen chloride (1M solution in diethyl ether) and then concentrated. The residue was crystallised from acetone to yield the title compound (E59) as a white powder (220 mg). MS electrospray (+ion) 377 (MH$^+$). $^1$H NMR δ (DMSO-d6): 10.62 (1H, s), 7.62 (2H, m), 7.40-7.25 (4H, m), 7.08 (2H, m) 4.82 (4H, m), 4.64 (1H, m), 3.81-3.58. (1H, m), 3.45-3.20 (2H, m), 2.95 (2H, m), 2.38-1.62 (10H, m).

EXAMPLE 60

N-{4-[(1-Cyclobutyl-4-piperidinyl)oxy]benzoyl}-5-fluoro-isoindoline hydrochloride (E60)

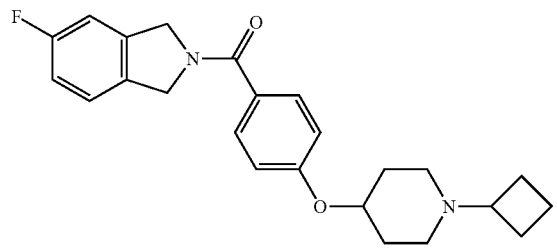

A stirred mixture of 4-[(1-cyclobutyl-4-piperidinyl)oxy]benzoyl chloride hydrochloride (D25) (0.20 g) and diethylaminomethyl polystyrene (3.2 mmol/g, 0.80 g) in DCM (10 ml) at rt was treated with 5-fluoroisoindoline (0.101 g) and stirred for 16 h. The reaction mixture was chromatographed directly [silica gel, step gradient 0-10% MeOH (containing 10% 0.880 ammonia solution) in DCM)]. Fractions containing the required product were evaporated, redissolved in DCM, treated with excess hydrogen chloride (1 M solution in diethyl ether) and then concentrated. The residue was crystallised from acetone to yield the title compound (E60) as a white powder (150 mg). MS electrospray (+ion) 395 (MH$^+$). $^1$H NMR δ (DMSO-d6): 10.60 (1H, s), 7.62 (2H, m), 7.42-7.06 (5H, m), 4.85 (4H, m), 4.66 (1H, m), 3.75-3.55 (1H, m), 3.45-3.20 (2H, m), 2.90 (2H, m), 2.41-1.62 (10H, m).

EXAMPLE 61

N-[2-Chloro-4-(3-Piperidin-1-ylpropoxy)benzoyl]isoindoline hydrochloride (E61)

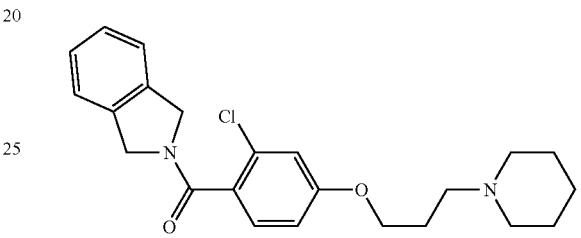

A stirred mixture of 2-chloro-4-(3-piperidin-1-ylpropoxy) benzoyl chloride hydrochloride (D28) (0.10 g) and diethylaminomethyl polystyrene (3.2 mmol/g, 0.8 g) in DCM (10 ml) at rt was treated with isoindoline (0.031 g) and stirred for 16 h. The reaction mixture was chromatographed directly [silica gel, step gradient 0-10% MeOH (containing 10% 0.880 ammonia solution) in DCM]. Fractions containing the required product were evaporated, redissolved in DCM, treated with excess hydrogen chloride (1M solution in diethyl ether) and then concentrated. The residue was crystallised from acetone to yield the title compound (E61) as a white solid (0.083 g). MS electrospray (+ion) 399/401 (MH$^+$). $^1$H NMR δ (DMSO-d6): 9.90 (1H, s), 7.41 (2H, m), 7.28 (3H, m), 7.11 (1H, s), 7.02 (1H, m), 4.83 (2H, s), 4.50 (2H, s), 4.14 (2H, t, J=5.9 Hz), 3.45 (2H, m), 3.25 (2H, m), 2.90 (2H, m), 2.18 (2H, m), 1.87-1.30 (6H, m).

EXAMPLE 62

N-{2-Chloro-4-[(1-isopropyl-4-piperidinyl)oxy]benzoyl}isoindoline hydrochloride (E62).

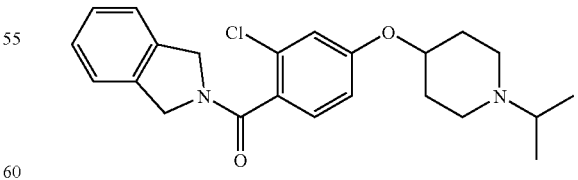

A stirred mixture of 2-chloro-4-[(1-isopropyl-4-piperidinyl)oxy]benzoyl chloride hydrochloride (D33) (0.20 g) and diethylaminomethyl polystyrene (3.2 mmol/g, 1.0 g) in DCM (10 ml) at rt was treated with isoindoline (0.08 g) and stirred for 16 h. The reaction mixture was chromatographed directly [silica gel, step gradient 0-10% MeOH (containing 10%

0.880 ammonia solution) in DCM]. Fractions containing the required product were evaporated, redissolved in DCM, treated with excess hydrogen chloride (1M solution in diethyl ether) and then concentrated. The residue was crystallised from acetone to yield the title compound (E62) as a white solid (0.09 g). MS electrospray (+ion) 399/401 (MH⁺). ¹H NMR δ (DMSO-d6): 10.90 (1H, s), 7.33-7.10 (6H, m), 6.96 (1H, m), 4.82-4.51 (3H, m), 4.39 (3H, m), 3.35 (2H, m), 3.00 (2H, m), 2.11-1.80 (4H, m), 1.17 (6H, m).

EXAMPLE 63

N-{2-Chloro-4-[(1-isopropyl-4-piperidinyl)oxy]benzoyl}-5-fluoro-isoindoline hydrochloride (E63)

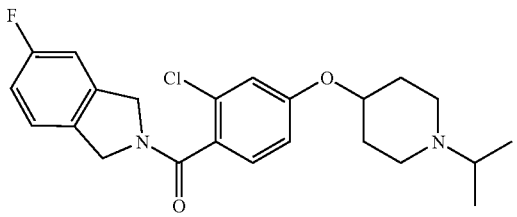

A stirred mixture of 2-chloro-4-[(1-isopropyl-4-piperidinyl)oxy]benzoyl chloride hydrochloride (D33) (0.20 g) and diethylaminomethyl polystyrene (3.2 mmol/g, 1.0 g) in DCM (10 ml) at rt was treated with 5-fluoroisoindoline hydrochloride (D8) (0.10 g) and stirred for 16 h. The reaction mixture was chromatographed directly [silica gel, step gradient 0-10% MeOH (containing 10% 0.880 ammonia solution) in DCM]. Fractions containing the required product were evaporated, redissolved in DCM, treated with excess hydrogen chloride (1M solution in diethyl ether) and then concentrated. The residue was crystallised from acetone to yield the title compound (E63) as a white solid (0.09 g). MS electrospray (+ion) 417/419 (MH⁺). ¹H NMR δ (DMSO-d6): 9.80 (1H, s), 7.22-6.81 (6H, m), 4.70-4.39 (3H, m), 4.25 (3H, m), 3.24 (2H, m), 2.88 (2H, m), 2.10-1.70 (4H, m), 1.06 (6H, m).

EXAMPLE 64

N-{2-Chloro-4-[(1-cyclobutyl-4-piperidinyl)oxy]benzoyl}isoindoline hydrochloride (E64)

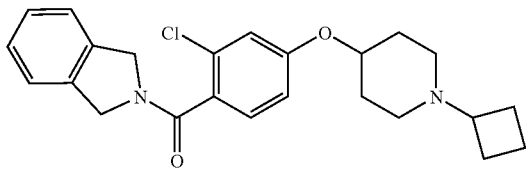

A stirred mixture of 2-chloro-4-[(1-cyclobutyl-4-piperidinyl)oxy]benzoyl chloride hydrochloride (D36) (0.20 g) and diethylaminomethyl polystyrene (3.2 mmol/g, 1.0 g) in DCM (10 ml) at rt was treated with isoindoline (0.08 g) and stirred for 16 h. The reaction mixture was chromatographed directly [silica gel, step gradient 0-10% MeOH (containing 10% 0.880 ammonia solution) in DCM]. Fractions containing the required product were evaporated, redissolved in DCM, treated with excess hydrogen chloride (1M solution in diethyl ether) and then concentrated. The residue was crystallised from acetone to yield the title compound as a white solid (0.08 g). MS electrospray (+ion) 411/413 (MH⁺). ¹H NMR δ (DMSO-d6): 10.55 (1H, s), 7.45 (2H, m), 7.27 (4H, m), 7.11 (1H, m), 4.89-4.68 (3H, m), 4.52 (2H, m), 3.67 (1H, m), 3.46-3.18 (2H, m), 2.90 (2H, m), 2.40-1.63 (10H, m).

EXAMPLE 65

N-{2-Chloro-4-[(1-cyclobutyl-4-piperidinyl)oxy]benzoyl}-5-fluoro-isoindoline hydrochloride (E65)

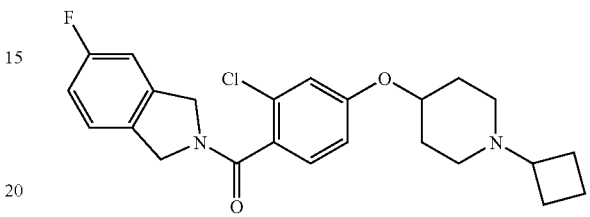

A stirred mixture of 2-chloro-4-[(1-cyclobutyl-4-piperidinyl)oxy]benzoyl chloride hydrochloride (D36) (0.20 g) and diethylaminomethyl polystyrene (3.2 mmol/g, 0.8 g) in DCM (10 ml) at rt was treated with 5-fluoroisoindoline hydrochloride (D8) (0.10 g) and stirred for 16 h. The reaction mixture was chromatographed directly [silica gel, step gradient 0-10% MeOH (containing 10% 0.880 ammonia solution) in DCM]. Fractions containing the required product were evaporated, redissolved in DCM, treated with excess hydrogen chloride (1M solution in diethyl ether) and then concentrated. The residue was crystallised from acetone to yield the title compound (E65) as a white solid (0.14 g). MS electrospray (+ion) 430/432 (MH⁺). ¹H NMR δ (DMSO-d6): 10.48 (1H, s), 7.46-7.06 (6H, m), 4.88-4.60 (3H, m), 4.51 (2H, m), 3.80-3.55 (1H, m), 3.46-3.18 (2H, m), 2.88 (2H, m), 2.38-1.64 (10H, m).

Preparation of Precursors

Certain precursors referred to in the preparation of the above Examples were prepared from the following references:

Substituted isoindolines: 5-Fluoroisoindoline (W. Adcock et al., Aust J Chem 1976, 29, 2571), 5-methoxyisoindoline and 5-trifluoromethoxyisoindoline (N E Austin et al., Bioorg Med Chem Lett., 2001, 11, 5, 685), 5-nitroisoindoline (Fraenkel, Chem Ber 1900, 33, 2811).

Substituted 1,2,3,4-tetrahydroisoquinolines: 6-cyano-1,2,3,4-tetrahydroisoquinoline (WO9850363, SmithKline Beecham), 7-cyano-1,2,3,4-tetrahydroisoquinoline (WO9850364, SmithKline Beecham). Preparation of additional substituted 1,2,3,4-tetrahydroisoquinolines: G E Stocker, Tet. Lett., 1996, 37 (31), 5453.

Substituted benzazepines: 7-cyano-2,3,4,5-tetrahydro-1H-3-benzazepine, 7-acetyl-2,3,4,5-tetrahydro-1H-3-benzazepine and 7-methylsulfonyl-2,3,4,5-tetrahydro-1H-3-benzazepine (WO0021951, SmithKline Beecham, N E Austin et al., Bioorg Med Chem Lett., 2000, 10, 22, 2553). 1-Aryl-2,3,4,5-tetrahydro-1H-3-benzazepines (J. Med Chem., 1986, 29 (11), 2315).

| Abbreviations | |
|---|---|
| Boc | tert-butoxycarbonyl |
| EtOAc | ethyl acetate |
| h | hour |

-continued

Abbreviations

| | |
|---|---|
| min | minutes |
| DCM | dichloromethane |
| MeOH | methanol |
| rt | room temperature |
| DCC | dicyclohexylcarbodiimide |
| DMF | dimethylformamide |
| IPA | isopropanol |
| TFA | trifluoroacetic acid |
| HOBT | 1-hydroxybenzotriazole |
| EDC | 1-(3-dimethylaminopropyl)-3-ethylcarbodiimide hydrochloride |

All publications, including but not limited to patents and patent applications, cited in this specification are herein incorporated by reference as if each individual publication were specifically and individually indicated to be incorporated by reference herein as though fully set forth.

Biological Data

A membrane preparation containing histamine H3 receptors may be prepared in accordance with the following procedures:

(i) Generation of Histamine H3 Cell Line

DNA encoding the human histamine H3 gene (Huvar, A. et al. (1999) Mol. Pharmacol. 55(6), 1101-1107) was cloned into a holding vector, pCDNA3.1 TOPO (InVitrogen) and its cDNA was isolated from this vector by restriction digestion of plasmid DNA with the enzymes BamH1 and Not-1 and ligated into the inducible expression vector pGene (InVitrogen) digested with the same enzymes. The GeneSwitch™ system (a system where in transgene expression is switched off in the absence of an inducer and switched on in the presence of an inducer) was performed as described in U.S. Pat. Nos. 5,364,791; 5,874,534; and 5,935,934. Ligated DNA was transformed into competent DH5α $E.$ $coli$ host bacterial cells and plated onto Luria Broth (LB) agar containing Zeocin™ (an antibiotic which allows the selection of cells expressing the sh ble gene which is present on pGene and pSwitch) at 50 µg ml$^{-1}$. Colonies containing the re-ligated plasmid were identified by restriction analysis. DNA for transfection into mammalian cells was prepared from 250 ml cultures of the host bacterium containing the pGeneH3 plasmid and isolated using a DNA preparation kit (Qiagen Midi-Prep) as per manufacturers guidelines (Qiagen).

CHO K1 cells previously transfected with the pSwitch regulatory plasmid (InVitrogen) were seeded at 2×10e6 cells per T75 flask in Complete Medium, containing Hams F12 (GIBCOBRL, Life Technologies) medium supplemented with 10% v/v dialysed foetal bovine serum, L-glutamine, and hygromycin (100 µg ml$^{-1}$), 24 hours prior to use. Plasmid DNA was transfected into the cells using Lipofectamine plus according to the manufacturers guidelines (InVitrogen). 48 hours post transfection cells were placed into complete medium supplemented with 500 µg ml$^{-1}$ Zeocin™.

10-14 days post selection 10 nM Mifepristone (InVitrogen), was added to the culture medium to induce the expression of the receptor. 18 hours post induction cells were detached from the flask using ethylenediamine tetra-acetic acid (EDTA; 1:5000; InVitrogen), following several washes with phosphate buffered saline pH 7.4 and resuspended in Sorting Medium containing Minimum Essential Medium (MEM), without phenol red, and supplemented with Earles salts and 3% Foetal Clone II (Hyclone). Approximately 1×10e7 cells were examined for receptor expression by staining with a rabbit polyclonal antibody, 4a, raised against the N-terminal domain of the histamine H3 receptor, incubated on ice for 60 minutes, followed by two washes in sorting medium. Receptor bound antibody was detected by incubation of the cells for 60 minutes on ice with a goat anti rabbit antibody, conjugated with Alexa 488 fluorescence marker (Molecular Probes). Following two further washes with Sorting Medium, cells were filtered through a 50 µm Filcon™ (BD Biosciences) and then analysed on a FACS Vantage SE Flow Cytometer fitted with an Automatic Cell Deposition Unit. Control cells were non-induced cells treated in a similar manner. Positively stained cells were sorted as single cells into 96-well plates, containing Complete Medium containing 500 µg ml$^{-1}$ Zeocin™ and allowed to expand before reanalysis for receptor expression via antibody and ligand binding studies. One clone, 3H3, was selected for membrane preparation.

(ii) Membrane Preparation from Cultured Cells

All steps of the protocol are carried out at 4° C. and with pre-cooled reagents. The cell pellet is resuspended in 10 volumes of buffer A2 containing 50 mM N-2-hydroxyethylpiperazine-N'-2-ethanesulfonic acid (HEPES) (pH 7.40) supplemented with 10e-4M leupeptin (acetyl-leucyl-leucyl-arginal; Sigma L2884), 25 µg/ml bacitracin (Sigma B0125), 1 mM ethylenediamine tetra-acetic acid (EDTA), 1 mM phenylmethylsulfonyl fluoride (PMSF) and 2×10e-6M pepstain A (Sigma). The cells are then homogenised by 2×15 second bursts in a 1 litre glass Waring blender, followed by centrifugation at 500 g for 20 minutes. The supernatant is then spun at 48,000 g for 30 minutes. The pellet is resuspended in 4 volumes of buffer A2 by vortexing for 5 seconds, followed by homogenisation in a Dounce homogeniser (10-15 strokes). At this point the preparation is aliquoted into polypropylene tubes and stored at −70° C.

Compounds of the invention may be tested for in vitro biological activity in accordance with the following assays:

(I) Histamine H3 Binding Assay

For each compound being assayed, in a white walled clear bottom 96 well plate, is added:

(a) 10 µl of test compound (or 10 µl of iodophenpropit (a known histamine H3 antagonist) at a final concentration of 10 mM) diluted to the required concentration in 10% DMSO;

(b) 10 µl $^{125}$I 4-[3-(4-iodophenylmethoxy)propyl]-1H-imidazolium (iodoproxyfan) (Amersham; 1.85 MBq/µl or 50 µCi/ml; Specific Activity ~2000 Ci/mmol) diluted to 200 pM in assay buffer (50 mM Tris(hydroxymethyl)aminomethane buffer (TRIS) pH 7.4, 0.5 mM ethylenediamine tetra-acetic acid (EDTA)) to give 20 pM final concentration; and (c) 80 µl bead/membrane mix prepared by suspending Scintillation Proximity Assay (SPA) bead type WGA-PVT at 100 mg/ml in assay buffer followed by mixing with membrane (prepared in accordance with the methodology described above) and diluting in assay buffer to give a final volume of 80 µl which contains 7.5 µg protein and 0.25 mg bead per well—mixture was pre-mixed at room temperature for 60 minutes on a roller. The plate is shaken for 5 minutes and then allowed to stand at room temperature for 3-4 hours prior to reading in a Wallac Microbeta counter on a 1 minute normalised tritium count protocol. Data was analysed using a 4-parameter logistic equation.

(II) Histamine H3 Functional Antagonist Assay

For each compound being assayed, in a white walled clear bottom 96 well plate, is added:

(a) 10 µl of test compound (or 10 µl of guanosine 5'-triphosphate (GTP) (Sigma) as non-specific binding control) diluted to required concentration in assay buffer (20 mM N-2-Hydroxyethylpiperazine-N'-2ethanesulfonic acid (HEPES)+100 mM NaCl+10 mM MgCl$_2$, pH7.4 NaOH);

(b) 60 μl bead/membrane/GDP mix prepared by suspending wheat germ agglutinin-polyvinyltoluene (WGA-PVT) scintillation proximity assay (SPA) beads at 100 mg/ml in assay buffer followed by mixing with membrane (prepared in accordance with the methodology described above) and diluting in assay buffer to give a final volume of 60 μl which contains 10 μg protein and 0.5 mg bead per well—mixture is pre-mixed at 4° C. for 30 minutes on a roller and just prior to addition to the plate, 10 μM final concentration of guanosine 5' diphosphate (GDP) (Sigma; diluted in assay buffer) is added;

The plate is incubated at room temperature to equilibrate antagonist with receptor/beads by shaking for 30 minutes followed by addition of:

(c) 10 μl histamine (Tocris) at a final concentration of 0.3 μM; and (d) 20 μl guanosine 5' [γ35-S] thiotriphosphate, triethylamine salt (Amersham; radioactivity concentration=37 kBq/μl or 1 mCi/ml; Specific Activity 1160 Ci/mmol) diluted to 1.9 nM in assay buffer to give 0.38 nM final.

The plate is then incubated on a shaker at room temperature for 30 minutes followed by centrifugation for 5 minutes at 1500 rpm. The plate is read between 3 and 6 hours after completion of centrifuge run in a Wallac Microbeta counter on a 1 minute normalised tritium count protocol. Data is analysed using a 4-parameter logistic equation. Basal activity used as minimum i.e. histamine not added to well.

Results

The compounds of Examples E1-E49 were tested in the histamine H3 functional antagonist assay and exhibited $pK_b$ values $\geq 7.5$. In particular, Examples E1-2, E4-12, E15-19, E21-31, E33, E35-36, E38-39, E41-42, E44-45, E47, E50-51, E54-55, E59-61 and E64-65 exhibited $pK_b$ values $\geq 8.5$.

What is claimed is:

1. A compound of formula (I) or a pharmaceutically acceptable salt thereof:

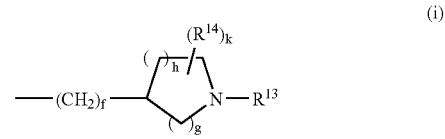

wherein:
$R^1$ and $R^2$ independently represent halogen, hydroxy, cyano, nitro, oxo, halo$C_{1-6}$ alkyl, polyhalo$C_{1-6}$ alkyl, halo$C_{1-6}$ alkoxy, polyhalo$C_{1-6}$ alkoxy, $C_{1-6}$ alkyl, $C_{1-6}$ alkoxy, aryl$C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkanoyl, $C_{1-6}$ alkoxycarbonyl, aryl, heteroaryl, heterocyclyl with 4-7 membered monocyclic saturated or partially unsaturated aliphatic ring containing 1 to 3 heteroatoms selected from oxygen or nitrogen, aryl$C_{1-6}$ alkyl, heteroaryl$C_{1-6}$ alkyl, heterocyclyl$C_{1-6}$ alkyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, arylsulfonyl, arylsulfonyloxy, arylsulfonyl$C_{1-6}$ alkyl, aryloxy, —CO-aryl, —CO-heterocyclyl, —CO-heteroaryl, $C_{1-6}$ alkylsulfonamido$C_{1-6}$ alkyl, $C_{1-6}$ alkylamido$C_{1-6}$ alkyl, arylsulfonamido, arylaminosulfonyl, arylsulfonamido$C_{1-6}$ alkyl, arylcarboxamido$C_{1-6}$ alkyl, aroyl$C_{1-6}$ alkyl, aryl$C_{1-6}$ alkanoyl, or a group $NR^{15}R^{16}$, —$NR^{15}CO$-aryl, —$NR^{15}CO$-heterocyclyl, —$NR^{15}CO$-heteroaryl, —$CONR^{15}R^{1-6}$, —$NR^{15}COR^{16}$, —$NR^{15}SO_2R^{16}$ or —$SO_2NR^{15}R^{16}$, wherein $R^{15}$ and $R^{16}$ independently represent hydrogen or $C_{1-6}$ alkyl;

wherein said aryl, heteroaryl and heterocyclyl groups of $R^1$ and $R^2$ may be optionally substituted by one or more substituents which may be the same or different and which are selected from halogen, $C_{1-6}$ alkyl, $C_{1-6}$ alkoxy, oxo, $CF_3$, $OCF_3$, $CN$, $C_{1-6}$ alkanoyl, $C_{1-6}$ alkylsulfonyl, $C_{1-6}$ alkylsulfonyloxy, $C_{1-6}$ alkylamido or $C_{1-6}$ alkylsulfonamido;

a and b independently represent 0, 1 or 2, such that a and b cannot both represent 0;

══ is a single or double bond;

$R^3$ represents halogen, $C_{1-6}$ alkyl, $C_{1-6}$ alkoxy, cyano, amino or trifluoromethyl;

m and n independently represent 0, 1 or 2;

p represents an integer from 0 to 3, such that when p is an integer greater than 1 two $R^1$ groups may instead be linked to form a heterocyclyl group;

$R^4$ represents —$(CH_2)_q$—$NR^{11}R^{12}$ or a group of formula (i):

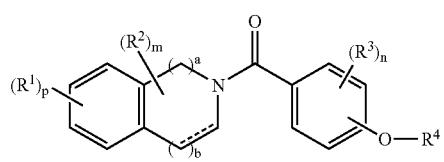

wherein q is 2, 3 or 4;

$R^{11}$ and $R^{12}$ independently represent $C_{1-6}$ alkyl or together with the nitrogen atom to which they are attached represent an N-linked heterocyclic group optionally substituted by one or two $R^{17}$ groups;

$R^{13}$ represents hydrogen, $C_{1-6}$ alkyl, $C_{3-8}$ cycloalkyl, —$C_{1-6}$ alkyl-aryl or heterocyclyl;

$R^{14}$ and $R^{17}$ independently represent halogen, $C_{1-6}$ alkyl, halo$C_{1-6}$ alkyl, OH, di$C_{1-6}$ alkylamino or $C_{1-6}$ alkoxy;

f and k independently represent 0, 1 or 2;

g is 0, 1 or 2 and h is 0, 1, 2 or 3, such that g and h cannot both be 0;

or solvates thereof.

2. A compound as defined in claim 1 wherein $R^1$ represents halogen, hydroxy, cyano, nitro, —$NR^{15}R^{16}$, —$NR^{15}COR^{16}$, polyhalo$C_{1-6}$ alkyl, heterocyclyl, $C_{1-6}$ alkyl, $C_{1-6}$ alkoxy, $C_{1-6}$ alkylsulfonyl, $C_{1-6}$ alkylsulfinyl, $C_{1-6}$ alkanoyl, arylsulfonamido, arylaminosulfonyl, —$NR^{15}SO_2R^{16}$, —$SO_2NR^{15}R^{16}$, —$CO$-heterocyclyl or two $R^1$ groups are linked to form a heterocyclyl group.

3. A compound as defined in claim 2 wherein p represents 1 and $R^1$ represents fluoro or cyano.

4. A compound as defined in claim 1 wherein m represents 1 and $R^2$ represents $C_{1-6}$ alkyl, aryl$C_{1-6}$ alkyl, aryl or heteroaryl.

5. A compound as defined in claim 1 wherein n represents 1 and $R^3$ represents halogen or polyhalo$C_{1-6}$ alkyl.

6. A compound as defined in claim 1 wherein $R^4$ represents —$(CH_2)_q$—$NR^{11}R^{12}$, q represents 3 and $NR^{11}R^{12}$ represents unsubstituted piperidine.

7. A compound according to claim 1 which is selected from the group consisting of:
N-[4-(3-Piperidin-1-ylpropoxy)benzoyl]indoline;
N-[4-(3-Piperidin-1-ylpropoxy)benzoyl]-3,4-dihydro-1H-isoquinoline;

N-[4-(3-Piperidin-1-ylpropoxy)benzoyl]-5-bromoindoline;
N-[4-(3-Piperidin-1-ylpropoxy)benzoyl]indole;
5-Fluoro-2-methyl-N-[4-(3-piperidin-1-ylpropoxy)benzoyl]-indole;
5-Methoxy-2-methyl-N-[4-(3-piperidin-1-ylpropoxy)benzoyl]-indole;
N-[4-(3-Piperidin-1-ylpropoxy)benzoyl]-5-fluoroindoline;
(±)-N-[4-(3-Piperidin-1-ylpropoxy)benzoyl]-2-methylindoline;
N-[4-(3-Piperidin-1-ylpropoxy)benzoyl]-1,2,3,4-tetrahydroquinoline;
N-[4-(3-Piperidin-1-ylpropoxy)-benzoyl]-5-nitroisoindoline;
N-[4-(3-Piperidin-1-ylpropoxy)-benzoyl]-5-aminoisoindoline;
N-[4-(3-Piperidin-1-ylpropoxy)-benzoyl]-5-(1-succinimido)-isoindoline;
N-[4-(3-Piperidin-1-ylpropoxy)-benzoyl]-5-(2-oxo-pyrrolidin-1-yl)-isoindoline;
N-[4-(3-Piperidin-1-ylpropoxy)-2-trifluoromethyl-benzoyl]isoindoline;
N-[4-(3-Piperidin-1-ylpropoxy)benzoyl]-6-cyano-1,2,3,4-tetrahydroisoquinoline;
N-[4-(3-Piperidin-1-ylpropoxy)benzoyl]-7-cyano-1,2,3,4-tetrahydroquinoline;
N-[4-(3-Piperidin-1-ylpropoxy)benzoyl]-2,3,4,5-tetrahydro-1H-3-benzazepine;
N-[4-(3-Piperidin-1-ylpropoxy)benzoyl]-7-methylsulfonyl-2,3,4,5-tetrahydro-1H-3-benzazepine;
N-[4-(3-Piperidin-1-ylpropoxy)benzoyl]-3,3-dimethylindoline;
N-[4-(3-Piperidin-1-ylpropoxy)benzoyl]-5-methoxy-6-trifluoromethyl-indoline;
N-[4-(3-Piperidin-1-ylpropoxy)benzoyl]-5-(dimethylaminosulfonyl)-indoline;
N-[4-(3-Piperidin-1-ylpropoxy)benzoyl]-5-(methylsulfinyl)-indoline;
N-[4-(3-Piperidin-1-ylpropoxy)benzoyl]-5-(methylsulfonyl)-indoline;
N-[4-(3-Piperidin-1-ylpropoxy)benzoyl]-5-acetyl-indoline;
(±)-N-[4-(3-Piperidin-1-ylpropoxy)benzoyl]-2-methyl-1,2,3,4-tetrahydroquinoline;
N-[4-(3-Piperidin-1-ylpropoxy)benzoyl]-6-methyl-1,2,3,4-tetrahydroquinoline;
(±)-N-[4-(3-Piperidin-1-ylpropoxy)benzoyl]-1-benzyl-1,2,3,4-tetrahydroquinoline;
(±)-N-[4-(3-Piperidin-1-ylpropoxy)benzoyl]-1-phenyl-6,7-dimethoxy-1,2,3,4-tetrahydroquinoline;
N-[4-(3-Piperidin-1-ylpropoxy)benzoyl]-6,7-dimethoxy-1,2,3,4-tetrahydroquinoline;
N-[4-(3-Piperidin-1-ylpropoxy)benzoyl]-5-(phenylsulfonamido)-1,2,3,4-tetrahydroquinoline;
N-[4-(3-Piperidin-1-ylpropoxy)benzoyl]-7-(phenylaminosulfonylyl)-1,2,3,4-tetrahydroquinoline;
(±)-N-[4-(3-Piperidin-1-ylpropoxy)benzoyl]-1-phenyl-1,2,3,4-tetrahydroquinoline;
N-[4-(3-Piperidin-1-ylpropoxy)-benzoyl]-5-methoxy-isoindoline;
N-[4-(3-Piperidin-1-ylpropoxy)-benzoyl]-5-trifluoromethylisoindoline;
N-[4-(3-Piperidin-1-ylpropoxy)benzoyl]-7-methoxy-2,3,4,5-tetrahydro-1H-3-benzazepine;
N-[4-(3-Piperidin-1-ylpropoxy)benzoyl]-7-acetyl-2,3,4,5-tetrahydro-1H-3-benzazepine;
N-[4-(3-Piperidin-1-ylpropoxy)benzoyl]-7-acetylamino-8-methoxy-2,3,4,5-tetrahydro-1H-3-benzazepine;
N-[4-(3-Piperidin-1-ylpropoxy)benzoyl]-7-methylsulfonamido-8-methoxy-2,3,4,5-tetrahydro-1H-3-benzazepine;
N-[4-(3-Piperidin-1-ylpropoxy)benzoyl]-6,7,8,9-tetrahydro-5H-[1,3]dioxolo[4,5-h][3]benzazepine;
(±)-N-[4-(3-Piperidin-1-ylpropoxy)benzoyl]-1-phenyl-6,7-dimethoxy-2,3,4,5-tetrahydro-1H-3-benzazepine;
(±)-N-[4-(3-Piperidin-1-ylpropoxy)benzoyl]-1-phenyl-8,9-dimethoxy-2,3,4,5-tetrahydro-1H-3-benzazepine;
(±)-N-[4-(3-Piperidin-1-ylpropoxy)benzoyl]-1-phenyl-7,9-dimethoxy-2,3,4,5-tetrahydro-1H-3-benzazepine;
(±)-N-[4-(3-Piperidin-1-ylpropoxy)benzoyl]-1-phenyl-7-hydroxy-8-methylsulfonyl-2,3,4,5-tetrahydro-1H-3-benzazepine;
(±)-N-[4-(3-Piperidin-1-ylpropoxy)benzoyl]-1-(4-methoxyphenyl)-6,9-dimethoxy-2,3,4,5-tetrahydro-1H-3-benzazepine;
(±)-N-[4-(3-Piperidin-1-ylpropoxy)benzoyl]-1-thienyl-7,8-dimethoxy-2,3,4,5-tetrahydro-1H-3-benzazepine;
N-[4-(3-Piperidin-1-ylpropoxy)benzoyl]-6-bromo-7,8-dimethoxy-2,3,4,5-tetrahydro-1H-3-benzazepine;
(±)-N-[4-(3-Piperidin-1-ylpropoxy)benzoyl]-1-(4-i-propylsulfonyl)-6-chloro-7,8- dimethoxy-2,3,4,5-tetrahydro-1H-3-benzazepine;
N-[4-(3-Piperidin-1-ylpropoxy)benzoyl]-7-fluoro-1,2,3,4-tetrahydroisoquinoline;
N-[4-(3-Piperidin-1-ylpropoxy)benzoyl]-6-chloro-1,2,3,4-tetrahydroisoquinoline;
N-[4-(3-Piperidin-1-ylpropoxy)benzoyl]-7,8-dichloro-1,2,3,4- tetrahydroisoquinoline;
N-[4-(3-Piperidin-1-ylpropoxy)benzoyl]-8-chloro-1,2,3,4-tetrahydroisoquinoline;
N-[4-(3-Piperidin-1-ylpropoxy)benzoyl]-7-cyano-2,3,4,5-tetrahydro-1H-3-benzazepine;N-[4-(3-Piperidin-1-ylpropoxy)benzoyl]-4-fluoroisoindoline;
N-[4-(3-Piperidin-1-ylpropoxy)benzoyl]-5-cyanoisoindoline;
N-[4-(3-Piperidin-1-ylpropoxy)benzoyl]-5-[(pyrrolidin-1-yl)carbonyl]isoindoline;
N-[4-(3-Piperidin-1-ylpropoxy)benzoyl]-5-[(morpholin-4-yl)carbonyl]isoindoline;
N-[2-Chloro-4-(3-Piperidin-1-ylpropoxy)benzoyl]isoindoline;
N-{2-Chloro-4-[(1-isopropyl-4-piperidinyl)oxy]benzoyl}isoindoline;
N-{2-Chloro-4-[(1-isopropyl-4-piperidinyl)oxy]benzoyl}-5-fluoro-isoindoline;
N-{2-Chloro-4-[(1-cyclobutyl-4-piperidinyl)oxy]benzoyl}isoindoline; or
N-{2-Chloro-4-[(1-cyclobutyl-4-piperidinyl)oxy]benzoyl}-5-fluoro-isoindoline
or a pharmaceutically acceptable salt thereof.

8. A compound according to claim 1 which is selected from the group consisting of:
N-[4-(3-Piperidin-1-ylpropoxy)-benzoyl]-5-fluoroisoindoline;
N-{4-[(1-Cyclobutyl-4-piperidinyl)oxy]benzoyl}isoindoline; or
N-{4-[(1-Cyclobutyl-4-piperidinyl)oxy]benzoyl}-5-fluoro-isoindoline
or a pharmaceutically acceptable salt thereof.

9. A compound according to claim 1 which is N-[4-(3-piperidin-1-ylpropoxy)benzoyl]isoindoline or a pharmaceutically acceptable salt thereof.

10. A pharmaceutical composition which comprises the compound of formula (I) as defined in claim 1 or a pharmaceutically acceptable salt thereof and a pharmaceutically acceptable carrier or excipient.

11. A process for the preparation of a compound of claim 1 or a pharmaceutically acceptable salt thereof, which process comprises:

(a) reacting a compound of formula (II)

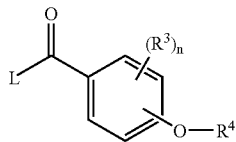

with a compound of formula (III)

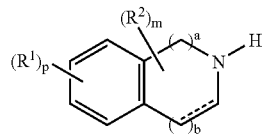

or a protected derivative thereof, wherein $R^1$, $R^2$, $R^3$, $R^4$, a, b, m, n and p are as defined in claim 1 and L is OH or a suitable leaving group; or (b) preparing a compound of claim 1 wherein $R^4$ represents —$(CH_2)q$—$NR^{11}R^{12}$ which comprises reacting a compound of formula (IV)

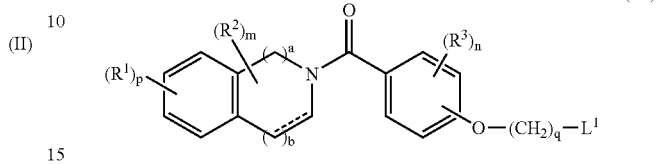

wherein $R^1$, $R^2$, $R^3$, a, b, m, n, p and q are as defined in claim 1 and $L^1$ represents a suitable leaving group with a compound of formula $HNR^{11}R^{12}$;

wherein $R^{11}$ and $R^{12}$ are as defined in claim 1; and optionally thereafter (c) deprotecting a compound of claim 1 which is protected; and optionally thereafter (d) interconversion to other compounds of claim 1.

* * * * *